United States Patent
Putnam et al.

(10) Patent No.: US 9,068,976 B2
(45) Date of Patent: Jun. 30, 2015

(54) INTEGRATED FILTRATION BIOANALYZER

(75) Inventors: David L. Putnam, Sammamish, WA (US); Jason A. Putnam, Sammamish, WA (US); Todd W. Hubbard, Seattle, WA (US); James A. van Zee, Seattle, WA (US)

(73) Assignee: PHOTONIC BIOSYSTEMS INC., Sammamish, WA (US)

( * ) Notice: Subject to any disclaimer, the term of this patent is extended or adjusted under 35 U.S.C. 154(b) by 685 days.

(21) Appl. No.: 12/582,392

(22) Filed: Oct. 20, 2009

(65) Prior Publication Data

US 2010/0129852 A1     May 27, 2010

Related U.S. Application Data

(60) Provisional application No. 61/106,624, filed on Oct. 20, 2008.

(51) Int. Cl.
| | | |
|---|---|---|
| *C12Q 1/02* | (2006.01) | |
| *G01N 33/52* | (2006.01) | |
| *C12Q 1/24* | (2006.01) | |
| *G01N 1/40* | (2006.01) | |

(52) U.S. Cl.
CPC ........ *G01N 33/52* (2013.01); *C12Q 1/24* (2013.01); *G01N 2001/4088* (2013.01)

(58) Field of Classification Search
CPC ........................................................ C12Q 1/24
USPC .................................................... 435/4, 7.21
See application file for complete search history.

(56) References Cited

U.S. PATENT DOCUMENTS

| | | | | |
|---|---|---|---|---|
| 2,904,474 | A | | 9/1959 | Förg .............................. 195/139 |
| 3,928,139 | A | | 12/1975 | Dorn ....................... 195/103.5 R |
| 4,336,337 | A | | 6/1982 | Wallis et al. .................. 435/292 |
| 5,081,017 | A | | 1/1992 | Longoria ......................... 435/30 |
| 5,420,017 | A | | 5/1995 | Tuompo et al. ................. 435/29 |
| 5,429,933 | A | | 7/1995 | Edberg ............................ 435/34 |
| 5,643,743 | A | | 7/1997 | Chang et al. |
| 5,861,270 | A | | 1/1999 | Nelis ............................... 435/34 |
| 5,972,641 | A | | 10/1999 | Øfjord et al. .................... 435/34 |
| 6,086,770 | A | * | 7/2000 | Matkovich .................... 210/645 |
| 6,287,849 | B1 | | 9/2001 | McNerney et al. |
| 6,302,860 | B1 | * | 10/2001 | Gremel et al. ............... 604/6.09 |
| 6,306,621 | B1 | | 10/2001 | Brenner et al. |
| 6,632,632 | B1 | * | 10/2003 | Lorentzen et al. ............. 435/34 |
| 6,670,145 | B2 | | 12/2003 | Brenner et al. ................. 435/29 |
| 2003/0082516 | A1 | | 5/2003 | Straus ............................... 435/4 |
| 2006/0263845 | A1 | | 11/2006 | Gu |
| 2007/0003997 | A1 | | 1/2007 | Kemmochi et al. ............ 435/34 |
| 2007/0281291 | A1 | | 12/2007 | Kuchta ............................. 435/4 |

OTHER PUBLICATIONS

Eisele, et al. "Evaluation of dyes in K-media for the enumeration of *Alicycclobacillus* spp. from apple juice", 2004, IFT Annual Meeting, abstract, 114C-2, 1 page.*
Hach Company, "Membrane filtration: coliforms, enterococci and pseudomonas", 2001, pp. 1-44.*
Hutter et al. "Evaluation of oxoplate for real-time assessment of antibacterial activities", Current Microbiology, 2004, 48:57-61.*
Angles, M.B., et al. 2000. Field evaluation of a semiautomated method for rapid and simple analysis of recreational water microbiological quality. Appl. Env. Microbiol. 66(10):4401-07.
Farnleitner, A.H., et.al. 2001. Rapid enzymatic detection of *Escherichia coli* contamination in polluted river water. Lett. Appl. Micro. 33:246-50.
Fiksdal, L. et.al. 1994. Monitoring of fecal pollution in costal waters by use of rapid enzymatic techniques. Appl. Environ. Microbiol. 60:1581-84.
Greenberg et al., Standard Methods for the Examination of Water and Wastewater, 8th edition, 1992. (Textbook).
International Search Report for PCT/US2009/005702, mailed Jul. 7, 2010.
Extended European Search Report issued in a related European Application No. 09822310.0, dated Apr. 3, 2012.

* cited by examiner

*Primary Examiner* — Bin Shen

(57) ABSTRACT

The present invention relates to an in vitro assay method and device that provides for detection and measurement of entities in a fluid sample that can be captured and concentrated in a unitized self-contained enclosed filter apparatus that is analyzed in an optical detection instrument for indications of the entity. It provides for analysis of biological material including cells, their enzymes, or other constituents thereof, that can be identified based on an indicator-generating means. The analysis provided for include detection of the presence of the entity, and changes in the entity over time, such as associated with growth and increasing metabolic activity with an expanding population of cells, or decreasing metabolic activity, for example, due to presence of inhibitory or toxic agents.

33 Claims, 16 Drawing Sheets

Limiting Dilutions -- Ecoli

Resorufin as a pH Reporter in an Acrodisc

INTEGRATED FILTRATION BIOANALYZER

CROSS-REFERENCE TO RELATED APPLICATIONS

This application claims the benefit of U.S. Provisional Application No. 61/106,624, which was filed on Oct. 20, 2008, hereby incorporated by reference.

STATEMENT REGARDING FEDERALLY SPONSORED RESEARCH

The U.S. Government owns rights in the present invention pursuant to contract number W81XWH-04-C-0149 from the United States Department of Defense through the US Army Medical Research Acquisition Activity.

BACKGROUND OF THE INVENTION

The present invention pertains to a set of devices and their related methods to rapidly and simply perform detection, quantitation, and identification of microorganisms in samples collected from a variety of sources including but not limited to drinking water, wastewater, industrial and pharmaceutical process waters or surface extraction solutions.

Diverse Needs & Requirements

There are diverse needs for microbiological tests and a diverse array of test methods and devices to assess their presence. In the US, municipal drinking water suppliers are required by the Environmental Protection Agency (EPA) to test for the presence of one *E. coli* or Total Coliforms in 100 mL of their product water. In Europe, tests require both identification and enumeration of these organisms' presence. Recreational water monitoring requires enumeration of *E. coli* and fecal coliforms from fresh water and *Enterococcus faecalis* from salt water with the United States Congress mandating detection in less than 4 hours. Protection of the food supply chain involves evaluating critical points in the preparation process where contamination is most likely to occur and where it will have the greatest impact. In these applications, no one test format is generally useful, and a need for greater test speed would benefit the ultimate application utility.

To meet the diverse needs of these applications, a variety of methods have been developed. Most notably, there is direct filtration and growth of the bacteria on a membrane, growth of bacteria in a solution and observation of a chemical change arising from their growth, and direct observation of the bacteria or some property of the bacteria in a solution using a developing agent. An ideal test method would be:
- simple to perform with a minimal number of handling steps
- capable of analyzing a sample of a milliliter or less or conversely up to a liter in volume
- sensitive to as few as one organism
- able to analyze more than one specific type of organism within a given sample
- able to detect and measure specific types of target organisms in the presence of large numbers of non-target organisms
- able to differentiate that organism(s) are alive and replicating rather than senescent or dead
- able to quantify the viable organisms present
- highly accurate with a low rate of false positives/false negative results
- able to complete an analysis and provide results within hours
- executable in an outdoor field environment, not requiring a laboratory or ancillary support equipment
- able to provide test results without requiring operator involvement after the test is initiated
- executable by minimally skilled operators
- small, portable, low power, and self-contained Direct observation of cells can be accomplished using a variety of methods as simple as turbidity or more sophisticated and specific methods using labeled antibodies directed at specific antigens on the cell surface. Using agglutination methods or lateral flow technology, the antigen-antibody method can be rapid, performed in the field and easily read by non-technical personnel. However, large numbers of organisms are typically required, and the methods are unable to differentiate viable from non-viable organisms. DNA technology can similarly provide a relatively rapid result. However, these techniques require highly trained personnel manipulating samples in a laboratory to achieve reproducible results, and it is still not possible to differentiate viable from non-viable organisms.

Filtration allows for concentration of a large volume water sample which can then be incubated with a number of different media to allow growth and identification of viable organisms. Detailed materials and methods are published in *Standard Methods for the Examination of Waste and Wastewater*. In these methods, a sample is typically filtered using a filter membrane held in a filter funnel. After filtration, the membrane is removed from the funnel, transferred to a culture plate containing growth media where it is incubated for typically for 24-48 hours. After the incubation period, colonies growing on the membrane can be identified through morphological-, biochemical-, antigenic- or DNA-fingerprinting analyses. The principle advantages of membrane filtration methodology are its ability to concentrate organisms from large volume samples and its ability to identify and quantify specific organisms from the sample. Obvious disadvantages of this method are the need to handle the membrane, which increases the potential for contamination, and the long incubation time. Devices have been contrived that minimize the need for filter handling after sample processing by integration of the filter membrane with a filter funnel and culture plate (e.g., Millipore, 55-Monitor); however, typical analysis times still require 24 hours of incubation.

In some applications (e.g., US drinking water tests), only a determination of the presence or absence of a viable indicator organism is required. Edberg [U.S. Pat. No. 5,429,933] discloses a simple assay for both the detection of coliforms and *E. coli* through the use of labeled metabolites and a highly enriched medium to promote the growth of injured microorganisms. The assay requires the addition of a prescribed volume of water to a vessel containing the dried culture medium and labeled metabolites. The vessel is incubated at the appropriate temperature for 18 hours, and the vessel is read for the presence of fluorescence and color to determine the presence of coliforms and/or *E. coli*.

The obvious advantage of this method is its simplicity; however, the method does not provide for quantification of the contamination level and still requires 18 hours of incubation. Other disadvantages to the method include: a narrow time window (18-26 hours) during which the sample must be observed; indeterminate color changes or obfuscation of the color by the sample's own color (e.g., iron containing water); the need to provide for a large incubator space and a waterbath (or other device with high heat transfer capability) for preheating the 100 mL of sample water to the required temperature in a short period of time.

Several workers in the field have proposed the use of an optical instrument to read changes in the optical indicator. Fiksdal ("Monitoring of fecal pollution in costal waters by use of rapid enzymatic techniques." Appl. Environ. Microbiol. 60:1581-84) proposed use of a fluorometer in 1994 to measure color changes in a sample resulting from β-galactosidase. In a related patent, Øfjord (U.S. Pat. No. 5,972,641) similarly proposed the use of a fluorometer to measure a sample's fluorescence after incubation for a prescribed time. In this method, a small aliquot of sample fluid was mixed with a growth media containing 4MU-galactopyranoside which is hydrolyzed by coliform bacteria to produce a fluorescent indicator of coliform activity. After 9 hours of incubation, an aliquot of the sample-media mixture is transferred to a cuvette, alkalinized with 2.5M NaOH then measured in a carefully calibrated fluorometer. If the sample's fluorescence is greater than a prescribed level, the sample is considered to be positive.

Øfjord's approach was later semi-automated in the Colifast CA-100 (Colifast Systems ASA). Methods and results using this system are reported by Angles ("Field evaluation of a semiautomated method for rapid and simple analysis of recreational water microbiological quality." Appl. Env. Microbiol. 66(10):4401-07). The instrument requires dedicated floor space, requires careful calibration against known fluorescent standards and requires measurement of a blank sample to estimate a detection threshold. Samples of 6 mL water (maximum sample size) were mixed with 6 mL concentrated media then incubated for 7 hours. Using a series of tubing and pumps, the machine withdraws a small aliquot every 100 minutes, adds NaOH to alkalinize the sample then measures its fluorescence. If the sample fluorescence exceeds the threshold level, it is considered positive. The test showed that highly contaminated samples could be rapidly assessed. However, the system was prone to cross-contamination from previous samples and it had a high rate of false positives, presumably due to background enzyme activity. Further, it was not possible to test larger sample volumes (e.g. >100 mL) which is needed to meet drinking and bottled water testing requirements.

Famleitner ("Rapid enzymatic detection of *Escherichia coli* contamination in polluted river water." Lett Appl. Micro. 33:246-50) describes using a filter to capture and concentrate a sample followed by measurement of fluorescence. In this work, the processed filter is removed from the filter funnel and added to a beaker containing growth media with the fluorescent-conjugate 4-methylumbelliferyl-β-glucuronide (4MU-glu) and incubated at 37° C. Aliquots were removed, alkalinized and measured for increases in fluorescence after 10 minutes, 20 minutes, and 30 minutes on a sophisticated benchtop fluorometer. Comparison with sample blanks and known fluorescence standards allowed the authors to quantify the rate of 4-MU production and subsequently to demonstrate a log-log relationship between the glucuronidase activity and the number of viable *E. coli* for organism concentrations greater than 1000 cfu/100 mL. No attempt to quantify below this level was reported. Consequently, although the method was fast, it had a number of drawbacks including its lack of sensitivity, laborious handling requirements, requirements for a lab based fluorometer with both positive and negative standards and a high likelihood for false positives at low contamination levels of *E. coli*.

Thus, a variety of prior art methods and devices have been devised to meet some testing requirements for the environmental, food, pharmaceutical and research communities. In general, they are laborious, prone to contamination, or they provide very limited information about the sample. Tests that measure viability of organisms typically require 24 hours of incubation before they can be interpreted. Faster tests will typically not distinguish between viable and non-viable organisms. Additionally, the faster tests require a large and expensive lab-based instrument which requires extensive calibration and testing of negative controls.

Accordingly, current practices and described art have shortcomings with respect to meeting the attributes of an ideal test as identified previously. There is a need in the art for a method and device that integrates the benefits of (i) membrane filtration in order to analyze large volume samples, (ii) incubation and culture of organisms in order to differentiate live cells and to expand the target from potentially a single cell to the level of a reliably measurable population, (iii) a single small disposable device that is easily prepared for analysis with minimal risk of contamination, and (iv) an automated detection method to rapidly identify indications of sample contamination by more than one type organism and quantify the numbers of organisms.

SUMMARY OF THE INVENTION

The present invention is for an in vitro assay method and device that provides for detection and measurement of entities in a fluid sample that can be captured and concentrated in a unitized self-contained enclosed filter apparatus that is analyzed in an optical detection instrument for indications of the entity. It provides for analysis of biological material including cells, their enzymes, or other constituents thereof, that can be identified based on an indicator-generating means. The analyses provided for include detection of the presence of the entity, and changes in the entity over time, such as associated with growth and increasing metabolic activity with an expanding population of cells, or decreasing metabolic activity, for example, due to presence of inhibitory or toxic agents.

The invention is preferably used for identification and quantification of microorganisms, in particular with analyses that require or are based on growth and propagation of the organisms. The method and filter apparatus for the collection of the organisms provides additionally for the culture of said organisms with concurrent optical analyses of the contents of the filter apparatus. The invention enables a simple means of preparing a fluid sample and the culturing of cells and their analysis, in the protection of the enclosed environment of the filter apparatus, which is vital to the assay as exposure to contaminant organisms external to the assay can invalidate the analysis. Said protection of the filtered sample for the analytical procedure is likewise importantly applicable to other fluid sample assays where contamination of the filtered entity is to be avoided, as is exposure of the user to the sample.

The scope of application is a filterable fluid sample and the in vitro analysis of test entities that can be removed from the fluid by filtration. The test entity can be molecules in a solution, particulate matter, or biological material, which includes microorganisms, cells and higher multi-cell organisms. Removal of the test entity by filtration processes includes any mode of separation whereby the entity can be captured, bound, and/or entrained by the filter element such that the test entity is selectively retained or immobilized and thereby concentrated from the fluid passed through the filter element.

The basis for the filter retention of the test entity can be chemical, biochemical, or physical properties of the entity, such as size or surface charge. Fluid can be moved past the filter-element preferably by negative-pressure, or vacuum based approach, applied to the outlet or discharge, or post-processed side of the filter apparatus so as to draw or pull fluid through from the inlet side. Alternatively, positive pressure can be employed to push fluid through the filter-element from the upstream, incoming feed, or inlet side.

In accordance with this invention, a means and method utilizing a filter membrane integrated into an enclosed assay cartridge is provided for the selective capture and detection of filterable entities in a single disposable device. A luminescent means and a luminescent reader device are used for detecting the activity of these filtered particles.

The enclosed filter assay cartridge preferably has an enclosed assay cartridge volume that is no more than 10× the void volume of the filter membrane and most preferably a volume of 100-300 uL. The filter device is suitable for microbial filtration and subsequent growth wherein the filter comprises a porous polymeric membrane selected from the group consisting of nitrocellulose or mixed cellulose esters, polyether sulfone, nylon, polycarbonate, and polyvinylidenedifluoride (PVDF). Preferably the membrane is composed predominately of material wettable by the sample fluid.

Flushing and filling of the Integrated Filter Assay Cartridge (IFAC) with selective media containing multiple fluorescent and/or chromogenic substrates can be accomplished by one of two methods. First, preparation of a "full-fill" device is achieved by exposing both sides of the filter to media, which allows for planktonic growth of the captured organisms. Indications of the presence or absence of the organism and kinetics of the reporter conversion are then measured. Second, preparation of a "half-fill" device is achieved by exposing only one side of the filter to media which allows growth of individual colonies of captured organisms that can be visually examined. This enables a visual evaluation of individual colonies and their enumeration in addition to the optical instrument analysis of the presence or absence of the organism and kinetics of the reporter conversion.

Preferably the use of fluorogenic β-D-glucuronide substrate such as resorufin-β-d-glucuronide or 4-MU-glucuronide allows the detection of the glucuronidase enzyme activity. Fluorgenic β-d-galactopyranoside substrate such as EHC-galactopyranoside or 4-MU-galactopyranoside is similarly used for the detection of the galactopyranosidase enzyme activity. Additionally, in cells growing on the filter membrane, chromogenic glucuronide substrate such as X-glucuronide was used for the detection of glucuronidase activity. Chromogenic galactopyranoside substrate such as Magenta-galactopyranoside was used for the detection of galactopyranosidase enzyme activity in cells growing on the filter membrane. Combinations of chromogenic and/or fluorogenic substrates for simultaneous visual and instrument detection of enzyme activity is also possible, and can be aided by increasing the buffer concentration in the enclosed filter apparatus.

Some assay applications require the media to contain selection agents, stimulating, inhibiting or toxic compounds. Agent examples useful for the selection of coliform bacteria in water samples include salt concentration, antibiotics, and detergents. Agents useful for selectively or specifically stimulating growth of microbial populations include chemokines, vitamins, and cofactors. However, incubation of the filtration apparatus at optimal temperatures may still be required for microbial growth.

The kinetic luminescence detection is utilized in three ways. First, initial signal levels can indicate instrument performance and errors such as, contaminated measurement wells, loose optical filters, and/or declining excitation sources. Second, the rate of signal change as a function of time ($1^{st}$ derivative of signal) is used for the indication of initial enzyme concentrations present in a sample. Third, the rate of the $1^{st}$ derivative signal change as a function of time ($2^{nd}$ derivative of signal) is used for indicating microbial growth.

The filtration cartridge contains a housing with inlet and outlet ports and a porous membrane interposed between these ports such that a fluid sample introduced into the housing via the inlet port must pass through the filter prior to exiting through the outlet port. The housing is preferably non-opaque to luminescence emissions and has adequate clarity for viewing purposes and visual interrogation. A vent is also included on the inlet chamber to allow gas exchange without risk of contamination.

The filtration apparatus enables the introduction as well as removal of reagents and culture media, incubation of the apparatus, and optical measurement of the apparatus contents, while protecting the contents from external contamination. Preferably the filtration apparatus provides for all of the above cited procedures that are to be performed after filtration without requiring the filter element and its contents within the filter apparatus be removed, transferred to another apparatus, or exposed to external contamination in order to conduct the subsequent procedures. The instrument providing for optical interrogation of the filter apparatus enables selectively the interrogation of different aspects of the filter apparatus, from different perspectives, such as an outlet chamber side or inlet chamber side, or preferably the interrogation of all of the contents of the filter apparatus simultaneously.

It is to be understood that both the foregoing general description and the following detailed description are exemplary and explanatory and are intended to provide further explanation of the invention as claimed.

Figure 1:
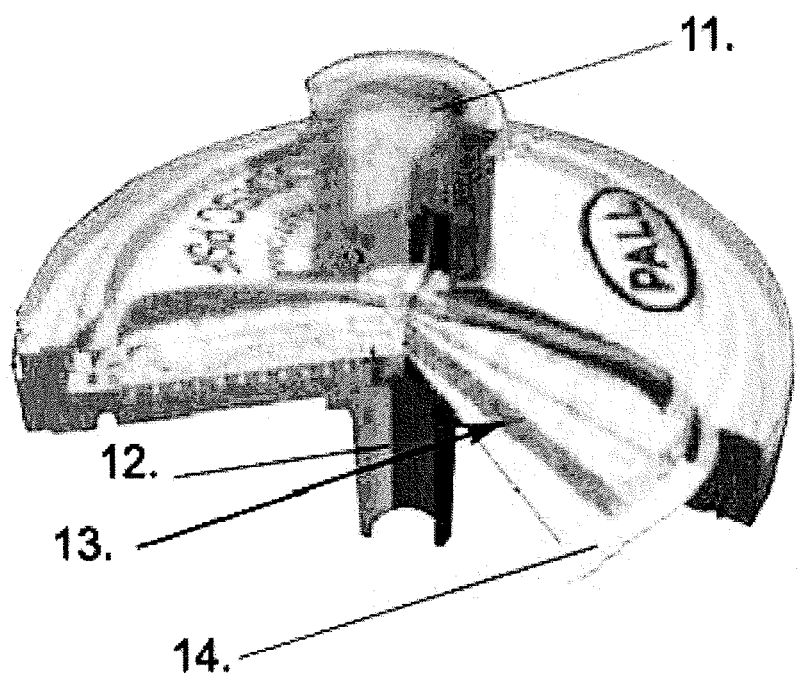
FIG. 1 is a syringe filter with a pre-filter in the inlet chamber. Ideally, the inlet chamber volume is less than 0.2 mL and the outlet chamber similarly has a volume of less than 0.2 mL. A membrane filter is bound to the housing (14) such that no leakage pathways are observed. Also pictured are inlet port (11), outlet port (12), and multi-layered prefilter (13).

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

The Integrated BioAnalyzer system is a product for conducting bioassays to detect the presence of live cells in a fluid sample, derive information about the number of cells present, and determine their functional status via measures of their metabolic activity.

In terms of testing for the presence/absence of cells, it can establish for instance whether a sample is contaminated, i.e., with bacteria (e.g., urinary infections), or is "clean"/sterile (e.g., filtered process-water). Applications aimed at assessing the number of cells in a test sample, or degree of contamination, are useful for instance in food-beverage testing (e.g., determining dairy product quality) and for monitoring efficacy of industrial hygiene practices (e.g., verifying sanitization).

Alternatively, tests can be designed with biological "indicator" cells put into the assay vessels in order to specifically test for the effects of inhibitory or stimulatory agents also included in the culture. In this category are toxicity tests such as antibiotic-sensitivity or resistance tests of infectious bacteria. Another example is the use of biological-indicator test samples to confirm the efficacy of sterilizer process killing of bacteria (e.g., hospital steam-autoclave cycles).

DEFINITIONS

The term "bacteria" as defined herein refers generally to single cell prokaryotes; for example bacteria from the genus *Esherichia* (e.g., *Esherichia coli* or *E. coli*), *Listeria*, *Salmonella*, *Seratia* or *Pseudomonas*. The term "Total Coliform" refers to a generally recognized group of gram-negative bacteria that ferment lactose and produce gas and includes bacteria from the genus *Escherichia*, *Klebsiella* and *Enterobacter*. More generally, the term "cells" can refer to both prokaryotic and eukaryotic cells and "cellular activity" refers to all processes that occur in a living cell, but most specifically, referring to metabolic processes including fermentation and respiration.

"Fluorescent conjugates," as described herein refer to compounds comprising a fluorescent reporter moiety and a nutrient moiety linked together by a covalent bond that is hydrolysable by specific enzymes. Preferably, the conjugated moiety is non-fluorescent, while hydrolysis of the bond releases a soluble fluorescent reporter moiety. Most preferably, the covalent linkage is chosen to be selective of specific enzyme systems present in the target organism. Fluorescent moieties should be chosen to have high extinction coefficients with excitation wavelengths suitable for stimulation with commercially available LEDs. Specific examples of such fluorescent reporters include the galactopyranoside and glucuronide conjugates of 4-methy umbelliferone and 4-trifluormethyl umbelliferone among others. Most preferably, ethyl- 7-hydroxycourmarin-4-carboxylate-galactopyranoside (EHC-gal) is used to indicate Total Coliforms including *E. coli* based on their galactosidase activity. Further, Resorufin-glucuronide is preferably used as the fluorescent indicator of *E. coli* based on its glucuronidase activity.

"Chromogenic conjugates," as described herein refer to compounds comprised of a highly colored moiety and a nutrient moiety linked together by a covalent bond that is hydrolysable by specific enzymes. The conjugated moiety should be colorless, but hydrolysis of the bond releases an insoluble, colored molecule clearly visible to the eye. Suitable chromogenic conjugates include the galactopyranoside and glucuronide conjugates of orthoNitro phenyl (ONP-), 5-bromo-4-chloro-3-hydroxyindole (X-), 6-Chloro-3-indolyl (salmon), 5-Bromo-6-chloro-3-indolyl (magenta-) among others. Preferred chromogenic conjugates are X-glucuronide for detection of *E. coli* and magenta-galactopyranoside for detection of Total Coliforms.

"Indicator means", as referred to herein generally includes signal or marker techniques as practiced in the art of optical detection for detecting the presence of an entity and for measuring said entity's cellular activity. Indicator means include fluorescent and chromogenic-conjugates capable of releasing a reporter molecule after enzymatic cleavage. They should also be construed to include luminescent tags and labeling techniques for specifically identifying an entity or its activity. These tags and techniques include but are not limited to fluorescent-labeled antibodies including micro/nano-particle labels and enzymatic based indicating reactions as engendered by Enzyme-Linked-Immuno-Assay methods and marker development with glucose-oxidase enabled means. Additionally, these indicator means should include means for measuring products of cellular function including oxygen consumption, pH shifts, NADPH or ATP production, measurable by optical elements included in the filter device.

"Growth media" utilized in the description herein refers to a fluid containing suitable components to support and promote growth and proliferation of preferred target cell types. Selective agents may be added to inhibit growth of undesirable non-target cells. A preferred embodiment utilizes detergents such as SDS or bile salts to inhibit the growth of gram-positive bacteria in an assay of coliforms. Further improvements utilize antibiotics or anti-fungal agents to further prevent growth of non-target organisms. Antibiotic examples include cefsoludin, ampicillin and antifungal agents include amphotericin B. pH buffering agents may also be included to prevent or mitigate pH changes occurring during growth of organisms. pH buffers can include both organic agents such as citrate or HEPES and non-organic buffers such as phosphate. Additionally, complex extracts can be included such as yeast extract, peptone digests or other complex extracts known to those practiced in the art. Additionally, the growth media may contain fluorogenic or chromogenic conjugates to aid in the detection of target organisms.

The term "Integrated Filter Assay Cartridge" (IFAC) refers to fluid filter devices characterized as having enclosed inlet and outlet fluid chambers with a filter membrane element separating the two chambers. A port to the inlet chamber allows introduction of fluid and a port on the outlet chamber allows evacuation of filtrate solution. Ideally, the chambers have small internal volumes, typically less than 10× the void volume of the filter membrane. An example of these devices includes syringe filters (e.g., Pall Acrodisc™).

Figure 2:
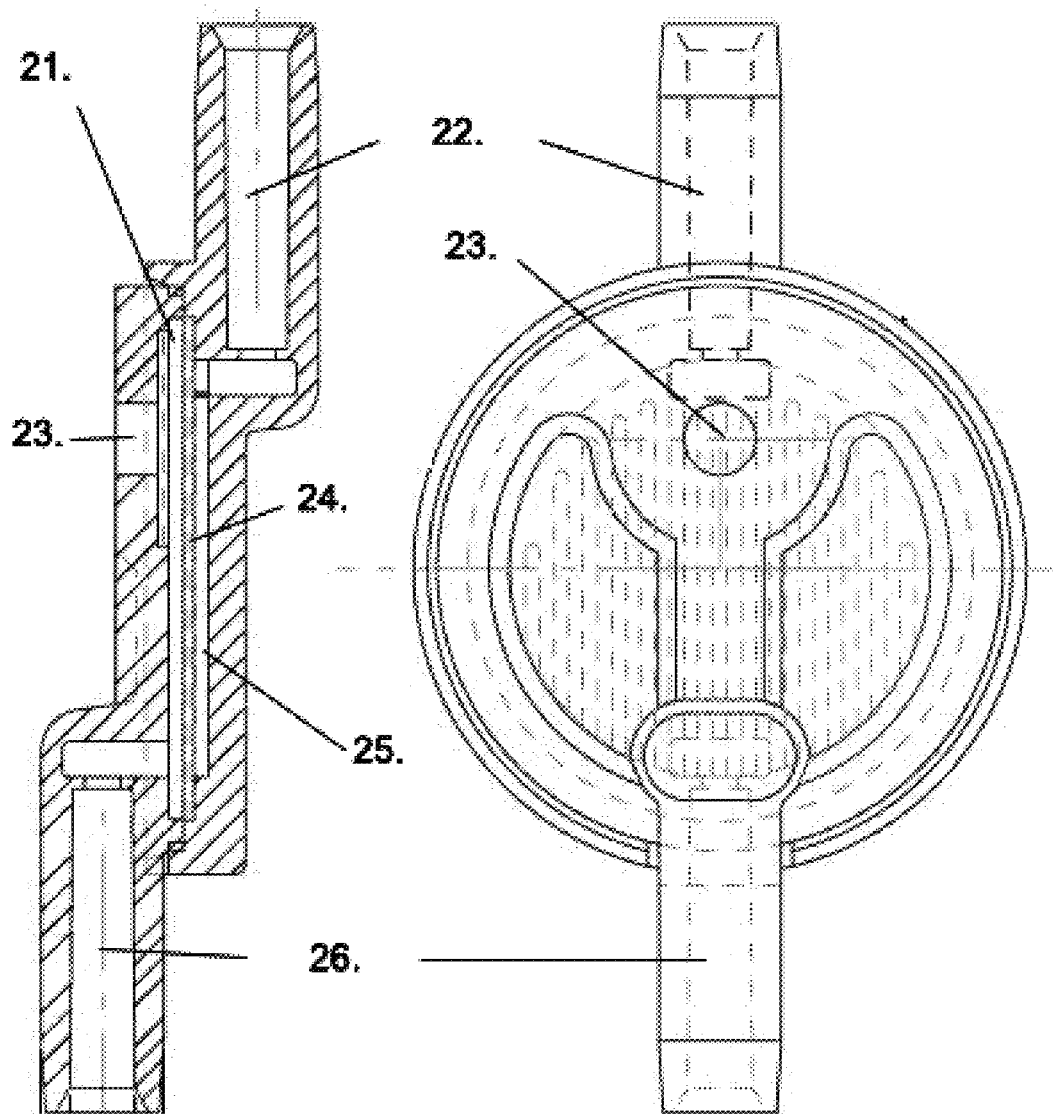
FIG. 2 depicts a μIV filter device for filtration, incubation and detection of filterable entities. The device's main features consist of an inlet port (26) and inlet chamber (21) separated from an outlet chamber (25) and port (22) by a porous hydrophilic filter (24). A vent port (23) in the inlet chamber (21) sealed with a porous hydrophobic material allows air to pass in and out of the chamber.

Preferably, the IFAC provides for a protected vent incorporated into an external wall of the inlet chamber. This is typically achieved by covering a small vent hole in the chamber wall with a gas-permeable hydrophobic membrane that allows gas to be pushed or pulled in or out of the chamber. A preferred design is a flat clear plastic cartridge with a fluid inlet-port on one end leading to an inlet chamber of small-volume. A hydrophilic porous filter membrane is held between the inlet chamber and a similarly small-volume outlet chamber with a corresponding outlet port. A schematic representation of an exemplary vented-cartridge-filter (VCF) is shown in FIG. 2. Exemplary devices include IV-filter cartridges such as those from Filtertek (Hebron, Ill.) and Borla (Torino, Italy).

The IFAC is intended to be both a collection filter as well as a growth chamber for the culture and assay measurement of target organisms. As such, after capture of the organisms, growth media is preferably supplied to support the target organism's growth in either of two configurations: Full-fill, or Half-fill.

The term "Full-fill" refers to an assay processing and testing configuration in which the IFAC is prepared having both the inlet and outlet chamber substantially filled with growth media. The inlet and outlet ports of these chambers can be filled or empty. The full-fill configuration allows for organism growth both on and in the filter membrane and in the fluid filled inlet chamber of the device. Preferably, the organisms will be impeded from growing in the outlet fluid chamber because they are restrained by the filter element.

The "Half-fill" configuration refers to processing and testing of the IFAC with growth media substantially confined to the outlet-chamber and outlet-port of the IFAC device for the growth period of the assay. Similar to membrane-filter based culture and assay techniques where the filter membrane is transferred to an absorbent pad filled with growth media after sample filtration, this inventive method bathes the cartridge's filter membrane with growth fluid in contact with the downstream side of the membrane. This provides for preferably visually distinct colonies to form on the surface of the filter membrane exposed to the inlet chamber and/or in the membrane, fed by the nutrients diffusing through the membrane from the media in the outlet chamber.

As described herein, the term "Rapid BioAnalyzer" (RBA) refers to a detection apparatus, an optical reader instrument capable of performing an analysis of prepared samples with no user intervention or interpretation required beyond insertion of the sample into the instrument. The instrument incubates Integrated Filter Assay Cartridge samples at a preset temperature and makes repeated optical measures of the sample's luminescent emission intensity over a period of several minutes to several days. The term "fluorescent signal" used herein is an arbitrary measure of the fluorescent intensity expressed as "counts." The instrument preferably utilizes two LED excitation sources and two emission detectors, making it possible to measure two or more appropriately chosen fluorescent indicators.

The Time to Detection (TTD) as used herein is the time after the start of incubation when growth is first detected by the instrument. Signal processing routines analyze changes in the sample's signal(s) and by using results from previously observed patterns, determine when the presence of viable target organisms is confirmed.

Integrated Bioassay Overview

The Integrated BioAssay (IBA) is an innovative combination of methods utilizing a small enclosed and unitized filter device, detection media, and an optical reader instrument for detecting the presence or analyzing a metabolic aspect of a filterable entity in a fluid solution. The IBA provides for a means to simplify analyses of a sample using filtration processes and methods that minimize sample contamination risks. Integration of the filter device with a small portable instrument provides for a means to conduct field testing. Integration of the filter device with robotics provides a means for automated testing. Novel reporter detection algorithms provide a means for routine test interpretation by personnel with minimal training.

In a general description of the invention, the test entity that is the object of the analysis can be molecules in a solution, particulate matter, or biological material including microorganisms, cells and higher multi-cellular organisms. The filtration processes include any mode of separation whereby the entity is selectively retained or immobilized and thereby concentrated from the fluid as said fluid passes through the filter apparatus. The basis for the filter retention of the test entity can be founded on chemical, biochemical, or physical properties of the entity, such as size, surface charge, or specific antibody-antigen, avidin-biotin, or carbohydrate-lectin interactions. Both the sample test fluid and reagents or assay fluids can be either pushed or pulled through the filter element by positive or negative pressure respectively to capture the test entity and prepare it for analysis in the IFAC. Incubation of the IFAC in the luminescent reader allows for both (i) holding the sample at a specific temperature and (ii) continuous optical measurement of chemical reactions occurring in the device that allow identification of the target entity.

Most commonly, the filter device is based on size selection and the filterable entity are cells, preferably microorganisms which are detected and measured on the basis of their metabolic activity. In a preferred embodiment the measurable indicator of their metabolism is a specific fluorescent-reporter conjugated to a sugar moiety that is a substrate of the target entity. The detection and measurement of the target entity is based on interpreting the kinetics of the fluorescent signal change associated with the release of the reporter, i.e., metabolism of the substrate by the target entity.

More specifically, the IBA is useful for testing 0.1 milliliter to 1 liter samples of water for the presence of coliform bacteria using fluorescent reporters with specific carbohydrate or amido hydrolysable linkages (e.g., 4MU-galactopyranoside or β-alanine-7amido-MU). By tracking the conversion rates of these fluorescent-conjugates, the IBA can rapidly detect the presence of viable microorganisms in a fluid sample. The IBA method utilizes a unique media formulation that combines ingredients for recovery of stressed organisms, promotion of rapid growth, and indicators of growth utilizing both fluorescent and chromogenic conjugates. A novel implementation of in-line filter cartridges provides for simpler handling, preparation of test samples, performance of membrane filtration procedures, and performance of either fluorescent bioassays or conventional visual observation of colony growth.

Another general implementation of the IFAC in an integrated bioassay approach utilizes oxygen sensors implemented in the enclosed filter cartridges to provide the indicating means for detecting and measuring cellular metabolism within the IFAC. The portable optical reader instrument provides incubation and continuous fluorescence measurements of the filter assay cartridges while detection and quantitation algorithms automatically differentiate and quantify fluorescent signal patterns indicative of viable versus non-viable organisms.

The principle steps of operation for the Integrated BioAssay system are to (i) filter a fluid sample in the IFAC, (ii) addition of culture media to the IFAC and its contents, (iii) simultaneous incubation and measurement of fluorescent signals indicative of metabolic activity in the IFAC, and (iv) automated determination of the number (or lack) of organisms in the IFAC. Additionally, the IFAC can be visually examined at some time after completion of the automated reading time for evidence of fluorogenic-substrate or chromogenic-substrate conversion with counting of visible colonies.

IBA Preferred Configurations

In the most preferred configuration and method, the IBA system is composed of three components defined previously including (i) the integrated filtration assay cartridge (IFAC), (ii) the growth media, and (iii) the assay instrument. By designing test methods that innovatively utilize the features of these three components, an integrated and a convenient test system has been invented.

Integrated Filter Assay Cartridge

The Integrated Filter Assay Cartridge (IFAC) design and utilization is one key to the assay-system function. While its features can be achieved utilizing individual components (e.g., a filter membrane for harvesting organisms from water, a culture vessel for incubating the filter), the IFAC combines a number of features into a novel assay device and method involving optical analyses. Some of the unique features enabled by the device include: (i) capture of organisms from microliter to liter volumes of fluid, (ii) concentration of test organisms into a small enclosed chamber that enables effective washing of the membrane and culture of the captured organisms without the need to manipulate the individual components. The compact size of the IFAC allows for easy handling, incubation and measurement of samples that could otherwise require large incubator cabinets to handle liters of fluid or many plates.

As defined previously, the IFAC is a disposable element to capture organisms from a fluid sample, concentrate the organisms into a small confined volume, and to further provide for their culture and concurrent analysis of growth and metabolic activity within the device. A preferred design uses 13 mm to 25 mm disposable syringe filters. Although a clear, non-fluorescent housing is preferable, other translucent materials, such as polypropylene, with only moderate optical clarity are acceptable. Similarly, non-fluorescing housing materials are preferred; however, materials with moderate fluorescence can be utilized.

Filter membranes are chosen from a wide variety of materials including but not limited to mixed cellulose esters (MCE), polypropylene, polyvinylidene chloride (PVDF), and polyether sulphone (PES). Preferably the filters should utilize an asymmetrical pore structure to maximize clogging resistance. Suitable pore sizes depend on the organism to be captured. The preferred pore sizes for most water sample applications are 0.45 um to 0.8 um depending on the desired flow rates, sample volume and turbidity, and tolerance for organism loss (pass-through).

One rendition of the Integrated Filter Assay Cartridges (IFAC) are syringe filters such as shown in FIG. 1. The device has an inlet and outlet port connected by a small volume chamber. A porous membrane filter separates the two chambers such that fluid entering the inlet must pass through the filter prior to exiting the device. The useful syringe filter has a filter surface area between 175 $mm^2$ and 500 $mm^2$ and most preferably is 13-25 mm in diameter with a flat filter membrane separating an inlet and outlet chamber. Larger diameter filter membranes can be used advantageously for larger volume separations.

Additionally, a large pore prefilter can be added to the inlet chamber of the IFAC to help remove materials from the fluid stream that would otherwise clog the smaller pores of the primary membrane filter situated downstream. The prefilter provides distinct advantages. By reducing clogging, it increases the rate of filtration and volume of fluid sample that can be typically processed. It increases the types of fluids that can be filter processed, in terms of degree of particulate loading. Fluid material that trapped in the pre-filter nonetheless contributes to the assay; it is not excluded from the analysis. Consequently, unlike an assay in which a separate prefiltration of the sample fluid is conducted before a final filtration onto the capture and assay filter, it is not necessary to have 100% pass-through of the target entity to the final filter element. Examples of preferred devices include the Pall Acrodisc™, Whatman Puradisc™, or other syringe filters known to those practiced in their use.

In a more preferred format, the IFAC is an adaptation of conventional microIV (μIV) or pediatric-IV filters currently used for medical applications (see FIG. 2). The filter has an inlet and outlet port with small volume chambers located on either side of a membrane filter. A valuable feature of this particular type of IFAC device is a hydrophobic vent located on the inlet chamber that is used to prevent "airlocking" of the filter. Air entering an enclosed inlet chamber from the fluid inlet path during fluid administration becomes trapped, and since it cannot pass through typical hydrophilic filter membranes once wet with fluid, it blocks fluid flow-through. In contrast, the special vented filter enables air that enters the inlet chamber to escape through the vent port. A schematic drawing of a μIV filter is shown in FIG. 2. Preferably, the inlet chamber volume is no more than 0.2 mL with a similar volume for the outlet chamber. The small volume chambers make it possible to effectively wash the filters with minimal volumes of buffer or to even omit wash steps altogether.

As an alternative preferred format, the filtering process within the IFAC is conducted by filtering a particle or physical element that can bind or attach to the biological material of interest. For instance, a particle, having a physical size much larger than a single microbe, can bind to particular biological organisms by chemical, biological, physical or other means and methods that are well known in the art of selectively separating certain organisms from complex fluids. Once bound, the larger particles and attached biological material, can be physically filtered and separated from unbound material. In contrast to the previously described preferred filtering method, the filter element pore-size need only be small enough to retain the large binding-particles, allowing smaller material and unbound organisms to pass through.

A further preferred filtering method is to separate material via a magnetic field. In the above example, a particle which possesses magnetic properties can be used, either larger or smaller than the organism it binds. These particles, and attached biological material, are filtered and retained within the IFAC by creating a magnetic field at the filter cartridge such that the particles and bound biomaterials are magnetically held in the IFAC as sample fluid flows through the IFAC. Non-magnetic materials and processed sample fluids are expelled from the IFAC. Subsequent assay is preferably performed on the filtered material.

Tubing attached to the inlet and outlet ports facilitate fluid administration through the inlet port, or attachment to a vacuum source at the outlet port in order to pull fluid through the filter device under negative pressure. In practical use, for sample filtration and fluid reagent introduction the outlet is attached to a vacuum line, pump, or manifold, and an inlet tube is inserted into the inlet port to serve as in inlet "pick-up" extension. Preferably the inlet tubing is a thin-walled, non-toxic polymer tube that can be easily inserted and removed prior to and after sample addition respectively. Alternatively, thin glass tubing has been utilized although breakage makes this option less desirable. A final alternative is to use no tubing at all.

Oxygen Sensitive Integrated Filter Cartridge (OxIFAC)

Incorporation of an oxygen-sensitive indicator means into the IFAC provides a simple, reagentless device capable of detecting metabolic activity of organisms trapped in the device. In the case of the Integrated BioAssay method and devices, the oxygen sensitive element is most preferably an optical device and sensor having spectral properties that depend upon the oxygen concentration and change in accord with changes in the oxygen concentration to which it is exposed. Inclusion of the oxygen sensitive element into the IFAC provides for rapid detection of oxygen changes either in the porous membrane or in the fluids contained in either of the fluid filled chambers or in the gas environment within either chamber. These oxygen changes are then readily applied to indicate the presence or absence of respiring organisms in the chamber or to measure their metabolic activity. In a manner consistent with the fluorescent-conjugates previously described, changes in the oxygen sensitive signal can be used to indicate the presence of live but senescent organisms or of actively dividing organisms. As an alternative to measuring the respiration of organisms, the IFAC and RBA device can be used to measure any oxidative enzyme in the cartridge. For example, taking advantage of the ability to perform secondary procedures after incubation of the IFAC, the addition of an antibody-labeled glucose oxidase to the sample with further incubation and optical analysis in the RBA will allow for sensitive and specific detection of a target entity.

The optical oxygen sensor is prepared by incorporating an oxygen sensitive optical dye into a suitable polymer. Oxygen sensitive dyes are ideally chosen from a group of luminescent molecules that exhibit quenching of their luminescent emissions in proportion to the oxygen concentration of their surrounding environment. Suitable dyes include metal-substituted porphyrins such as but not limited to PtTFPP, PtOEP, or PtTPP. These dyes can be incorporated into a wide range of polymers, chosen such that the dye is dissolved into the polymer matrix and such that oxygen diffusion into the domain surrounding the dye is limited. Candidate polymers include but are not limited to polycarbonate, polymethyl methacrylate, polyether sulphone, polyvinyl chloride, polypropylene, derivatives and copolymers of these polymers as well as materials derivatized with polymers such as cellulose acetate butyrate.

An oxygen sensitive integrated filter assay cartridge (OxIFAC) for an IBA assay can be prepared either by (i) incorporating a pre-dyed filter element into the filter cartridge, (ii) dying the filter element in the filter cartridge, or (iii) separately introducing an oxygen-sensitive sensor element that is a non-filter element into the IFAC during manufacturing or post-manufacturing prior to or during the assay phase.

Oxygen sensitive elements, including oxygen-sensitive porous-membrane filters, are prepared by inclusion of an oxygen-sensitive indicator dye in the polymer from which the element or porous-filter membrane is made during its manufacture. For example, the luminescent dye can be dissolved into a polymer slurry then cast as a film with subsequent extraction of pore-forming molecules. Alternatively, membranes can be formed by polymerization of the monomer solution with the luminescent dye included in the mixture. The oxygen sensitive filter membrane is then incorporated into the finished OxIFAC filter cartridge.

Alternatively, the oxygen sensing dye can be incorporated into the filter membrane after manufacture of the filter membrane or its final inclusion in the filter cartridge. This approach is based on an unexpected finding that oxygen sensitive dyes can be incorporated into the filter membrane of a syringe filter or IV-filter by first dissolving the dye into a solvent capable of penetrating and/or swelling the matrix/polymer of the filter membrane. The filter membrane is then exposed to the dye solution for a short period of time, which is performed with the membrane preferably before, or after, the filter membrane is fabricated into the filter cartridge. Upon completing the exposure to the dye solution the solvent is suctioned out of the filter membrane or the OxIFAC device. After a short drying period, the filter can be used for both filtration and measurement of oxygen changes in the IFAC. The unexpected finding with this approach was that (i) a solvent could be used to imbibe the dye into the structure of a porous filter element, in a manner that is essential for the dye to function as a useful sensor of oxygen; and (ii) that the solvent action necessary to convey the dye into the filter element, which was expected to degrade its structure, did not necessarily destroy the functionality of the filter element. It was discovered that by careful selection of the solvent, the oxygen-sensitive dye with suitable solubility in the solvent, the filter element with a limited sensitivity to the solvent, and exposure conditions limiting the duration of contact of the filter element with the solvent-dye solution, it was possible to create an oxygen-sensing filter membrane without significantly altering its porous structure and performance properties. The suitable conditions, most significantly the duration of exposure of the filter element to the solvent, must be defined for each given type of filter element material and given solvent through trials and assessments of the filter element performance characteristics, and changes thereof caused by the solvent treatment process.

For example, a preferred procedure for creating an OxIFAC from a fabricated syringe filter with a PES or a PVDF (polyvinyl difluoride) filter element was determined to be as follows. A solution of PtTFPP dissolved in methanol (0.1-0.01% w/v) was prepared. The dye solution was introduced to the internal chamber of IV-filter cartridges made with either PES or PVDF filter membranes exposing them to the solvent for 5 to 30 seconds at approximately 20° C. after which, the solution was suctioned off the membrane and out of the cartridge. The filter was allowed to dry for 24 hours at 37° C. We found that membrane filters with pores sizes of 0.2-0.8 microns treated in this manner nominally have the same particle retention capacity and flow rates as untreated filters and that the filters were capable of detecting oxygen changes occurring inside the OxIFAC.

The third approach for incorporating a non-filter oxygen-sensitive sensor element into the IFAC can be accomplished in two manners: one during manufacturing of the filter apparatus; the other post-manufacturing prior to or during the assay phase. In the former case, for example, an oxygen sensitive element, made by the inclusion of any indicator dye into a polymer by the methods described above, could be adhered or painted onto to one of the cartridge housing's internal aspects as a discrete independent sensor element prior to assembly of the filter cartridge. In a preferred case, dyed oxygen sensory films are incorporated into the filter device by the filter manufacturer.

Post-manufacture of the filter device, a preferred manner of converting a plain IFAC device into an oxygen sensory OxIFAC, is to prepare dyed oxygen-sensory particles that are introduced into the IFAC. Suitable particles with dye sequestered in polymers such as previously indicated can be made by a variety of techniques known in the practice for fabricating particles and powders. Particles, preferably made larger in size than will pass through the pores of the filter element in an IFAC, can be conveniently loaded and trapped within the device. The particles can be suspended in a fluid which is introduced into the IFAC as a component of a reagent, such as culture media, that is involved with the sample assay setup. In a preferred alternative mode of application, the particles are made smaller than the pores of the filter element, such that they will pass through it. However, by providing the particles with a binding property, such as an antibody coating or a chemical surface activation, which enables the particles to stick to the target entity or cells, then the particles can be selectively bound and retained within the IFAC. Unbound particles preferably pass through the device and can be washed away. Remaining bound particles then serve as a tag or reporter of the target entity, providing an oxygen-sensitivity indicator signal.

Growth Media—Coliform Testing

The growth media preferably contains components suitable to support and promote the growth of the target cells and suppress non-target cells in the IFAC. A preferred media composition for assay of E. coli and coliforms is shown in Table 1. In general, we find that any commercial growth media composition suitable for conventional membrane filtration can be used in the IBA format, however, inclusion of the components listed generally provides greater recovery of stressed organisms.

TABLE 1

Preferred components in PacTec coliform growth media

| Component | Min Conc | Max Conc |
|---|---|---|
| Carbon Sources | | |
| Lactose | 0.5 g/L | 3 g/L |
| Pyruvate | 0.5 g/L | 3 g/L |
| Resorufin-glucuronide | 25 mg/L | 100 mg/L |
| EHC-galactopyranoside | 100 mg/L | 500 mg/L |
| Extracts | | |
| Yeast Extract | 0.1 g/L | 2 g/L |
| Peptone no. 3 | 1 g/L | 3 g/L |
| Beef Heart | 0.1 g/L | 2 g/L |
| Salts, Buffers, Detergent, Antibiotics | | |
| NaH2PO4 | 400 | 1200 |
| KHPO4 | 500 | 800 |
| HEPES | 3 g/L | 6 g/L |
| NaCl | varies | varies |
| SDS | 50 mg/L | 200 mg/L |
| Bile Salts | 100 mg/L | 300 mg/L |
| Cefsoludin | 0.5 mg/L | 5.0 mg/L |
| Vitamins & Cofactors | | |
| RPMI-1640 (dehydrated - w/o glucose) | | |

Generally, glucose or other typically utilized carbohydrate sources are avoided when target organisms are selectively grown and measured via reporters using a culture medium employing fluorescent-conjugate based on carbohydrate substrates. To mimic the inductive effect on coliform recovery found with "milk-media," but avoid the addition of non-specific carbohydrates, lactose is added to the media. Our preferred fluorescent-conjugates composition utilizes Resorufin-glucuronide and EHC-galactopyranoside. The diffusible nature of these fluorescent reporter moieties is ideally suited for measurement by the fluorescent reader. Alternatively, 4-MU which has similar fluorescent excitation and emission wavelengths has been successfully utilized; however, its sensitivity to the fluid environment, in particular pH and ionicity, made the EHC-conjugate a preferred choice. Other reporters have been reported in literature and are generally known to those practiced in the art.

Complex extracts are preferably included in the media composition, such as yeast extract, peptone digests or other complex extracts known to those practiced in the art. Extracts provide complex sources of amino acids, B-vitamins, soluble vitamins and carbohydrates that are not readily synthesized. As a defined source of vitamins and cofactors, we have included RPMI-1640 without glucose (SIGMA) in our media. Although media using only RPMI was found to be adequate for recovery and growth promotion of freshly cultured microbes, samples with organisms held in water for over two weeks showed generally poor recovery with delayed detection times in the bioassay. Consequently, although the nature of these extracts is potentially variable, we have found their inclusion to be necessary for preferred performance of the bioassay.

In addition to the fluorescent-conjugates measured by the fluorescence reader device, the Integrated BioAssay method provides for use of insoluble chromogenic-conjugates for visually identifying colonies on the filter membrane after 18-24 hours of incubation. While visual identification is generally performed well after identification of growth by the fluorescent reader device, both the fluorogenic and chromogenic reporters can be used in the reaction media. Preferred reporters for Coliform testing utilize Resorufin-glucuronide and X-glucuronide to identify E coli with EHC-galactopyranoside and magenta-galactopyranoside to identify the Total Coliform population. Because the preferred fluorescent reporters are soluble, there is generally no optical interference between fluorogenic and chromogenic reporter systems. Alternate reporter combinations are also acceptable; however, it is preferable to use a chromogenic-galactopyranoside reporter (Total Coliform indicator) that does not obscure the E. coli indicating glucuronide reporter.

Selection criteria for the culture and measurement of target organisms can include physical criteria as well as chemical components included in the media. Incubation temperature has been effectively used in the IBA to select for fecal coliforms (44.5° C.) from environmental water samples and B. stearothermophilus (55° C.) in thermal sterilization biological indicators. The reader device provides for stable incubation of the samples at a preferred temperature while continuously measuring optical changes in the IFAC. It can also be appreciated that physical selection of target organisms can be conveniently accomplished by choice of the filter membrane pore size or surface properties as well.

The growth media utilized in the preferred format for coliform testing utilizes additional components to support and promote growth of cells as well as selective agents to inhibit growth of non-target cells. A preferred embodiment utilizes detergents such as SDS or bile salts to inhibit the growth of gram-positive bacteria in the coliform assay. Other assay improvements involving selective inhibition utilize antibiotics or anti-fungal agents to further prevent growth of non-target organisms. Antibiotic examples include cefsolu-din or ampicillin. Antifungal agents include amphotericin. Buffering agents are also preferably included in the media composition to prevent or mitigate media pH changes occurring during growth of organisms. pH buffers include both organic agents such as citrate or HEPES and non-organic buffers such as phosphate.

Rapid Bioanalyzer

The instrument is a key component of the Rapid BioAnalyzer system. It is designed to be robust, portable and capable of incubating and analyzing the contents of an IFAC either in the field or in a laboratory setting. The most useful measures are made by measuring changes in fluorescence occurring within the IFAC due to hydrolysis of the fluorogenic substrates by specific bacteria. After preparation and insertion of the sample into the instrument, no further action is required by the user.

The instrument incubates the samples at a preset temperature and makes repeated optical measures of the sample (e.g., fluorescence) over a period of preferably up to 24 hours. Based on specific detection algorithms, the instrument judges whether any changes in the optical signals measured for an IFAC over time indicate growth of organisms or simply background changes in sample fluorescence. Background signal changes can be due to either non-specific hydrolysis or degradation of a fluorescent-conjugate with release of the reporter, or for example due to cleavage of the fluorescent-conjugate due to enzymes present in non-viable organisms. The results determined by the instrument are reported to the user via a panel display indicating preferably the presence/absence of growth, the type of organism(s) identified, an estimate of the number of organisms predicted to have been present at the onset of the sample analysis, a relative measure of the activity associated with the sample or its rate of indicator change, and a plot of the fluorescence time curve. Specific data values can also be exported to a computer or other memory device.

Figure 3:
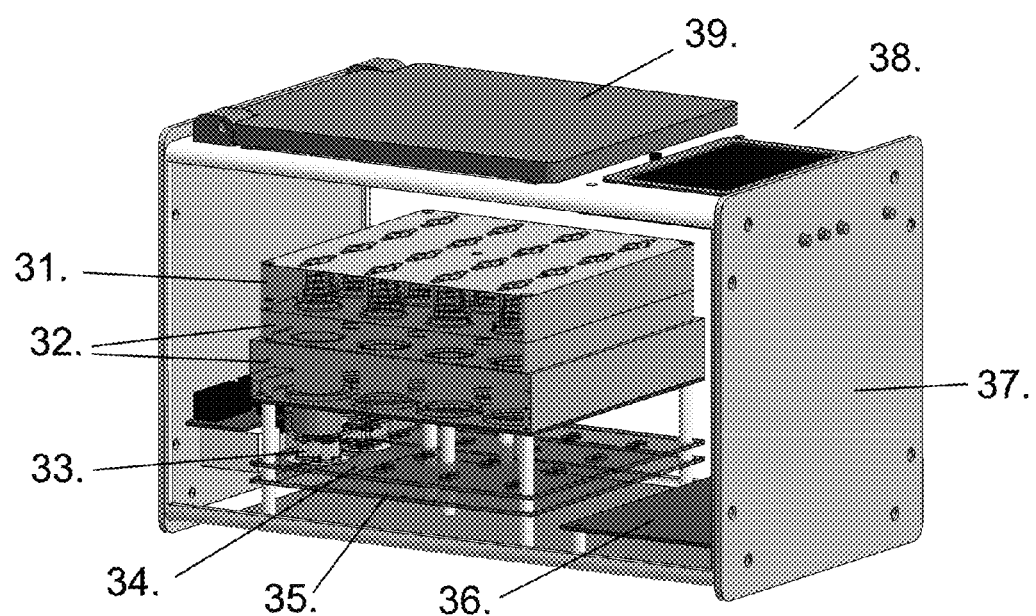
FIG. 3 is an embodiment of the Rapid BioAnalyzer instrument with side panels removed. The Integrated Filter Assay Cartridge block (31) is attached to heater blocks (32). LED's and detectors are contained in metal casing (33) attached to LED board (34). Detector board (35) is located directly below LED board (34). Main board (36) controls the overall function of the instrument. Front panel (37) contains status LEDs indicating test status. Display and touch screen (38) allows user interaction, and lid (39) allows access to test samples.
Figure 4:
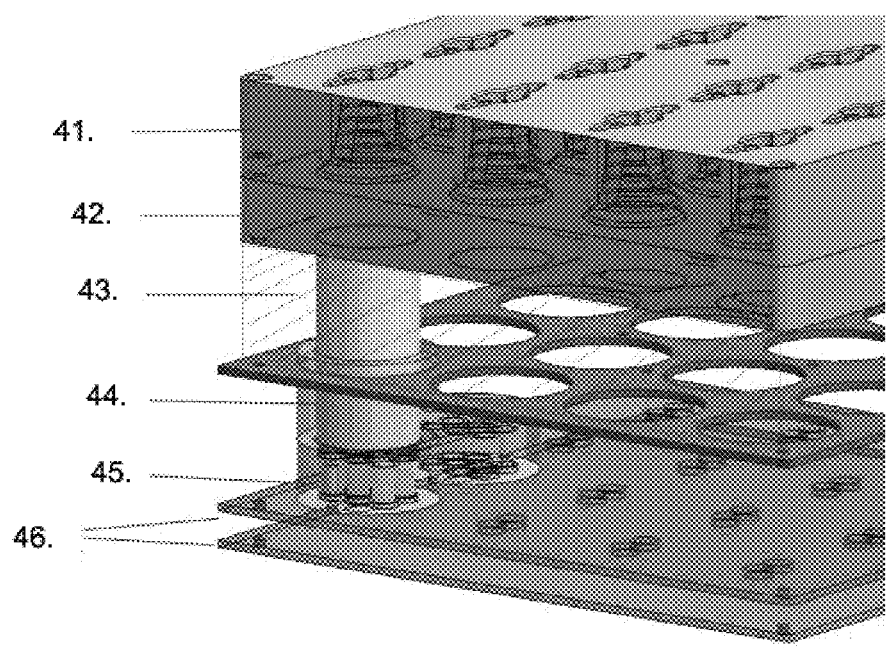
FIG. 4 is a schematic depiction of the Integrated BioAnalyzer heating and luminescence detection components. The Integrated Filter Assay Cartridge (IFAC) block (41) is integrally connected to a digitally temperature controlled heater block (42). A light pipe (43) is used to efficiently conduct excitation light from the LEDs to the IFAC sample and luminescent light from the IFAC to the photodetector. The LEDs and detectors are held in a metal casing (45), controlled by LED and detector circuit boards (46), and thermally connected to the heater block (42) to provide both thermal and electrical isolation from the ambient environment. Thermal stabilization for the LEDs is also provided by heater extension collar (44).

The RBA instrument shown in FIG. 3 is a fluorescence reader with the side panels removed. It is designed to run on either line power or batteries for operation in the field. The internal aspects of the optical path are shown in greater detail in FIG. 4 and described top to bottom as follows. An aluminum "optical" block (31) holds the IFAC in a thermally controlled chamber or well. Preferably, the internal aspects of the chamber provide reflective surfaces that help conduct light to and from the IFAC. More preferably, the reflective internal aspects provide the ability to read optical signals from one or both sides of the IFAC. This optical block is thermally connected to an aluminum heater block (32). This heater block utilizes temperature sensors and a proportional feedback controller to monitor and control resistive heating elements in this block to heat and maintain the block, i.e., sample incubation temperature, at a selected temperature. Preferably the incubation system components and the control circuitry keep the temperature of the IFAC sample while under assay to within +/−0.5° centigrade of the specified temperature setting.

The instrument uses LED's as light sources to optically interrogate the IFAC samples placed in the sample-holding chambers optical block, preferably for excitation of luminescent reporters in the IFAC. PIN photodiodes are used to measure the stimulated emissions derived from the IFAC reporters. Light pipes (33) are used to conduct light to and from the samples and the LED light sources and the photodiode detectors. Appropriate optical filters are used with the LED sources and the detectors to selectively limit both the excitation and emission wavelengths of the optical signal measurement in order to improve the instrument's sensitivity. The LEDs are preferably held in a thermally stabilized metallic housing (35) to minimize signal perturbations from thermal or electrostatic field changes.

In our preferred format, the RBA instrument's excitation LEDs and photodetectors are optically filtered to minimize stray light leakage. Preferably, stray light rejection between the source and detector is greater than $10^4$. For example, stimulation of a Resorufin fluorophore is accomplished using a 530 nm green LED optically filtered with a 3-cavity 535±30 nm FWHM interference filter. Measurement of its emission uses a PIN-photodiode with a 610 nm longwave pass filter (both from Intor Optical, NM). A transimpedance photodiode amplifier output is fed to a final signal measurement circuit.

We have employed several schemes for measuring the small signals, mostly well known to engineers designing instruments for small signal measurements. Each scheme has certain advantages depending on the luminescent measurement being made (e.g., fluorescence or phosphorescence) and on the expected ambient lighting conditions.

Scheme (1) uses a high-resolution (24-bit) delta-sigma converter. It was thought this might work well because such devices combine ('sum'='sigma') millions of small ('delta') measurements in a way that almost completely rejects line-frequency interference. The ADC is capable of resolving 0.3 µV making it possible to feed the photodiode (PD) output directly to the ADC's internal amplifier. This simple scheme produces good signal to noise if external light is eliminated.

Scheme (2) modulates the LEDs (and thereby the fluorescence signal), and responds only to the part of the signal that has the same modulation frequency. This scheme, known as Phase Sensitive Detection (PSD), is used in many commercial fluorimeters because of its ability to reject unwanted optical and electrical noise. This scheme was implemented using a Cypress Semiconductor PSOC (Programmable System On a Chip). PSOC devices combine a flexible set of analog 'building blocks' with a simple microprocessor, allowing one to 'custom build' in a small piece of silicon what was once a large circuit board. In this case we built two phase-and-frequency-adjustable oscillators, capable of producing either sine or square waves. One oscillator modulates the LEDs, while the other drives the 'dual-slope' switch, which serves as the 'de-modulator.' The frequency is adjustable from 500 Hz to 10000 Hz, and the phase relationship between the oscillators can be varied over a +/−225° range. This method has proven very sensitive in the RBA system due to its ability to reject ambient light (e.g., due to light leaks into the instrument box) and some electrical noise.

Scheme (3) uses an integrator circuit to build up a signal over a relatively long period of time. In this mode, the signal is accumulated during specific periods of time that are varied to maximize the noise free signal. In this manner, very small signals can be amplified much like a camera integrates light by increasing the time the shutter is open. Just like a camera, the integration times must be optimized for specific conditions to avoid noise (blurriness) and signal saturation (overexposure). This scheme is most practical for making phosphorescent measurements of the oxygen sensor lumiphores. In the phosphorescence mode, the LEDs are then turned on to charge up the phosphor indicator molecules, and then turned off to allow two or more rapid integrations of the phosphorescent decay. In all, the instrument integrates signal during three sequential periods (A, B, & C), each 10-40 ms long. By treating these measurements ratiometrically (i.e., using B/A and C/A, rather than A, B, C directly) the results tend to be independent of the signal light intensity.

The goal in the instrument's signal analysis design was to allow evaluation and interpretation of signal characteristics independent of the operator. Toward this end, the RBA utilizes various signal analysis algorithms to determine enzyme (e.g., glucuronidase) turnover rates and enzyme turnover rate changes positively identifying the presence of a target organism. Other signal characteristics allow estimation of the initial viable cell count. Additionally, the data can be compared to stored results from previous tests for evaluation of trends in the microbial populations. By providing a rich data stream of organism metabolic activity, we anticipate that with additional experience, the analyst will be able to mine further interpretations from this data.

As an example of the simplest data interpretation, we have found that while samples prepared with clean water and low numbers of lab-derived organisms will typically have low fluorescent-conjugate conversion rates and consequently low background fluorescent signals, environmentally sourced samples will commonly have very high rates of fluorescent reporter production not directly related to viable organisms present in the sample. These environmental samples may have high concentrations of enzymes in non-viable cells or in cells that do not grow in the selective media. As a consequence, these enzymes can lead to appreciable fluorescent signal changes over a 1-10 hour period, making it impractical to identify growth based on only a signal-intensity threshold or a single endpoint measurement value.

The IBA method takes particular advantage of the continuous fluorescent signal reading over time and acquisition of multiple measurement data-points on each sample during its incubation/assay. Time-derivatives of the fluorescent signals are calculated and analyzed to determine background enzyme activity in the sample. The first derivative is generally not associated with bacterial growth and enzyme activity specifically associated with growth. In contrast, the $2^{nd}$ derivative of the fluorescent signal as a function of time is highly correlated with growth of the organisms. Determining if a sample's fluorescent signal $2^{nd}$ derivative crosses a threshold provides a systematic method for identifying growth in a sample. Determination of the time when the $2^{nd}$ derivative crosses the threshold provides a Time to Detection (TTD) which in turn is characteristic of the samples starting concentration of target organisms (see example 1).

A critical determination for the instrument is to determine that a test sample does not contain the target organism (e.g., *E. coli* or Total Coliforms). It is well recognized that there will always be the possibility that a sample can contain viable organisms that either are not stimulated to grow in the test environment or only begin dividing after long periods of time in that test environment. The Integrated BioAnalyzer system uses two statistical concepts in determining if a sample does not contain the target organisms. First is the "NegaTime" which is defined as the time that a single target organism would be expected to be observed by the optical analyzer. The NegaTime thus implicitly includes instrument and assay configuration parameters as well as the growth characteristics for a typical target organism. The most important growth characteristics have been the lag time before an organism begins dividing and the doubling time for that organism in its logarithmic growth phase. The second statistical assumption is a "SafetyTime" which is defined as the amount of additional time over the NegaTime needed for most outlier organisms to become detectable. A typical NegaTime for one rendition of the IFAC and RBA when measuring *E. coli* is 480 minutes with a SafetyTime of 105 minutes. Using these parameters, the instrument will declare a test sample to be free of *E. coli* after 585 minutes of incubation with 99% confidence that the sample will not ultimately be deemed positive.

The instrument advantageously provides estimates for the number of viable organisms present at the start of the test using algorithms with teachable parameters. The quantitation algorithms innovatively compare the time that one target organism would be expected to give a positive result (termed the "NegaTime") and the actual observed time that a positive result is observed (i.e., the TTD). Dividing this time difference by an average doubling time, the number of viable organisms at the start of the assay can be estimated. The simple equation is shown below.

$$Ecoli = 2^{(NegaTime-TTD/DblTime)}$$

For the *E. coli* specific reporter Resorufin-glucuronide, the TTD can be used in a straight forward manner to estimate the number of *E. coli* present in the starting sample. Other specific, single organism reporters could be used to estimate starting numbers in a like manner.

Figure 5:
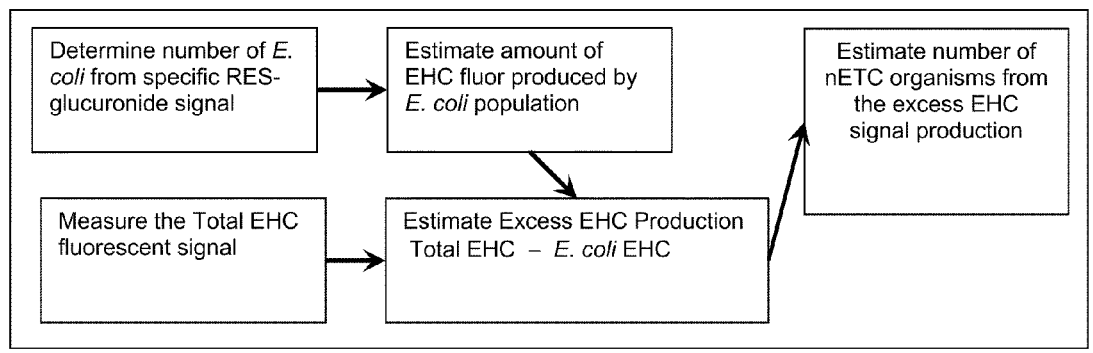
FIG. 5 shows a scheme for estimating the proportion of non-*E. coli* Total Coliforms when both *E. coli* and other Total coliforms are present.

In drinking water testing, it is desirable to determine the presence and number of Total Coliforms (TC) in a water sample. Additionally, it is highly desirable to determine subsets of this TC population, namely, both the *E. coli* and non-*E. coli* Total Coliforms (nEcTC) subsets. Both the *E. coli* and nEcTC populations will hydrolyse galactopyranoside conjugates (e.g., EHC-gal) and we do not know of any fluorescent-conjugate that can specifically detect the nEcTC population. However, an estimate of this population subset can be made using a subtractive methodology as shown in FIG. 5 for estimating the subset of non-*E. coli* Total Coliforms (nEcTC). In the example, Total Coliforms (both *E. coli* and nEcTC) are measured using the galactosidase reporter (EHC-gal) and the *E. coli* population is measured using the glucuronide reporter (RES-glu). Next, the *E. coli* population is estimated from the glucuronide reporter's TTD (glu-TTD) and the characteristic "negatime" and doubling-time for *E. coli*. Next, the TTD from the galactopyranoside (gal-TTD) is compared to the expected gal-TTD for that number of *E. coli* (calculated from previous testing with pure *E. coli* cultures). If the gal-TTD is shorter than the expected for *E. coli* alone, the number of nEcTC needed to make up the difference can be calculated.

The method works well if the nEcTC population exceeds the *E. coli* population by at least a factor of 10. Rapid replication and production of the EHC reporter tend to swamp out the nEcTC signal contribution for smaller differences. Additionally, it is well recognized that the nEcTC population is extremely heterogeneous and therefore, only an estimate using an "average" organism is calculated.

Alternate Rapid Bioanalyzer Embodiment

An alternative embodiment to the measurement apparatus is encompassed by utilizing an imaging device to analyze bacterial growth in filter apparatus samples. Its primary function is to take time-lapse digital photographs of the colony outgrowths within the filter apparatus and employ image analysis to measure biological material. The measurement apparatus fundamentally uses an image sensor to identify colony appearance, growth, and general activity. From the results, we can establish the degree of contamination of a liquid sample, and quantify the contamination based on the total number of discrete colonies arising. Additionally, we acquire valuable information about the rate and distribution profile of colony appearance.

In order to accomplish this, the measurement apparatus systematically captures time-lapse images of multiple samples throughout their incubation period. The device consists of: a CCD digital camera; a rotary stage which can support several filter apparatus, run with a small motor and simple control board; LEDs for color images and UV LED lights fitted with small barrier filters; UV photographic filter and macro lens; and an incubation chamber.

Within the device each filter apparatus sample is automatically positioned in front of the CCD camera and illuminated by white light. The image is captured and transferred to the computer for record keeping and image analysis. After the white LEDs are turned off, UV LEDs are turned on and another image of the same filter apparatus is captured and transferred to the computer for analysis and record keeping. The next sample is then indexed into position. This routine runs continuously, acquiring time-lapse image sequences for the duration of the test (usually 8-18 hours).

Upon completion, the analysis test report is examined. The device can also be programmed to remotely alert users when the first growth is detected so captured images can be immediately viewed from any location and action can be taken. The picture sequences provide short detection times and high sensitivity.

Non-Fluorescence Modes of Operation

Although luminescence detection (i.e., fluorescence and phosphorescence) is the preferred mode of operation for the RBA system, there are many cases where other modes of operation are beneficial. Analogous to the soluble fluorescent-conjugates identified above, soluble chromogenic-conjugates are commonly used in bioassays. For example, 6-o-β-galactopyranosyl-luciferin can be used as a bioluminescent indicator of galactosidase activity. Similarly, ortho-nitrophenyl-β-d-galactopyranoside (ONPG) produces an intense yellow colored solution signal after hydrolysis and is the basis for assays in water testing (IDEXX—Colilert™) molecular biology (SIGMA, β-galactosidase reporter gene activity kit), and hospital laboratories (SOP—UK Public Health Service) to name a few examples. Similar but related measures of turbidity changes are also commonly described in cellular and microbiological applications.

It is therefore in the scope and intention of the current invention to provide a means to address instrument measurement means for luminescence and absorbance. Luminescence detection is easily accomplished with the RBA by simply measuring the sample luminescence with the LED's turned off. In this case, the IBA takes advantage of the ability post-process samples in the IFAC. Briefly, a sample IFAC is incubated for a period of time to develop sufficient numbers of target organisms. The IFAC is then removed from the reader device and a developer solution is injected into the device which is then replaced in the reader. After an appropriate amount of time, the bioluminescence is read, either at a single time point or at multiple time points.

Absorbance/reflectance measures have been made either by (i) directly measuring absorption of light as it passes through the sample or (ii) indirectly by measuring changes in light intensity from a fluorescent emitter either included as a constituent of the sample assay solution, or incorporated as a component of the IFAC device, or built into the RBA optical path for measuring the IFAC. The fluorescent emitter is employed so that light from the source exciting its emission, or its emissions, must pass through the sample solution, such that the measured light is thereby sensitive to changes in absorbance of the sample solution that result in attenuation of the excitation or emitted light.

In the first case of direct measurements, the instrument is highly versatile in that LEDs and optical filters can be chosen such that incident light from the LEDs is matched to the absorption band of a chromophore which is matched to the passband of the detector element. The art of devising absorbance instruments is well known to those practicing spectroscopic measures.

In the second case of indirect measurements of absorption, the system is set-up such that a fluorophore's excitation or emission is modulated by changes in a chromophore located somewhere in the light path. As an example, a filter membrane is prepared to contain a red fluorescent compound readily measured by one of the detectors and excitable by the green LED. A water sample containing *E. coli* is added to the IFAC which is then filled with a growth media containing ONP-galactopyranoside. Incubation of the IFAC results in release of ONP which absorbs both the green LED's excitation light as well as the red-fluorophore's emission light. The observed decrease in red fluorescent signal is proportional to the absorbance by ONP in the sample. Similar arguments can be readily appreciated for fluorophores in solution together with the chromophores.

Description of the IFAC Utilization:

Detailed descriptions of several methods for IFAC usage are described in the examples. The general approach to IFAC utilization is relatively simple. First, the fluid sample is passed through the filter device using either positive or negative pressure. The sample is then washed with a sterile fluid, if deemed necessary. Growth media or assay reagent is introduced into the device after which the IFAC's ports are plugged.

Utilizing positive pressure, to express fluid through the filter device, the IFAC inlet port is connected to a sample container whose contents can then be compressed to dispel fluid. Examples of containers might include a pipette for small microliter to milliliter volumes, or flexible bags (IV bag or "bag-in-a-box") for larger volumes. Alternatively, the IFAC can be connected directly to a pressurized fluid line such as a household tap or reverse-osmosis purification unit. Other applicable positive-pressure delivery approaches are syringes and fluid-pump systems, commonly employed in a variety of types, such as diaphragm, rotary, and peristaltic pumps.

After sample introduction, the IFAC is disconnected from the sample container and a second container with sterile wash fluid is connected to the inlet port which is then flushed through the filter using either positive or negative pressure. A highly advantageous feature of the device is that relatively small volumes of flush fluid are required due to the small volume of the IFAC. We have found that volumes as small as 0.3 mL are adequate to remove interfering substances from 13 mm syringe filters. A particularly advantageous feature of the device is the ability to completely evacuate the inlet chamber of fluid and fill it with air using air to push any fluid remaining in the inlet chamber through the filter. When the chamber is evacuated after sample addition, there can be such a small amount of residual fluid remaining in the filter device that a specific washing step is typically not required. Growth media is similarly added to the IFAC using a small pipette to push fluid into the device. The outlet port is plugged with a sterile cap. More conveniently, a flexible plastic compound such as Critoseal™ is forced into the outlet port to effect the seal.

Utilizing negative pressure, the IFAC inlet port is connected with a fluid path to a sample container and the IFAC outlet port connected to a vacuum source. The sample container is most conveniently a graduated device to allow addition of the desired sample volume to the system. In a preferred format, the sample is then drawn through the IFAC until the entire volume has been filtered after which the vacuum is turned off. In the preferred procedure, a volume of wash fluid is then added to the empty sample container then flushed through the device. Growth media is similarly added and the IFAC device sealed.

A distinct advantage of the IFAC as an assay vessel over other test approaches utilizing bulk solution samples (e.g., IDEXX, Colilert™) is its ability to harvest and concentrate organisms from either a small or a large volume solution, removing the bulk of fluid volume, and removal of soluble moieties in the sample that could potentially interfere with growth of the organisms or their sensitive detection. Further, it is highly advantageous that the filtered sample can be further washed to reduce any residual or remaining soluble moieties to negligible concentrations. Because most interfering substances have been washed out of the system, large volumes of media are not required to dilute or neutralize untoward effects. Further, the small internal volume and enclosed nature of the IFAC further reduces the need for large volumes of media to maintain optimal growth conditions for the organisms.

Full-Fill & Half-Fill Configurations

We have found two media-fill configurations to be advantageous for use with the IFAC. Depending on the testing results desired, either configuration can be utilized.

The Full-fill configuration bathes the membrane with media on both sides of the membrane with several key advantages. The first is that the full-fill allows for planktonic growth of the organisms in solution thus avoiding crowding or other surface effects that could impede growth and production of reporters. The second is that the diffusible fluorescent reporters are distributed more uniformly in the assay device, typically resulting in much higher signal levels over the course of the test. The half-fill configuration leaves media in the outlet chamber only.

The half-fill configuration inventively takes advantage of a wetted hydrophilic filter-membrane's resistance to passage of gas. After flushing and filling the filter derive with media, the inlet chamber is evacuated of fluid, and filled with air. Because air cannot traverse the wetted filter membrane, fluid flow will stop, leaving an air filled inlet chamber and a fluid filled outlet chamber. Sealing the outlet port prevents media from flowing back through the membrane into the inlet chamber. Microbes captured in the filter membrane grow into colonies on its surface (on the air filled inlet side) in a manner similar to that of conventional membrane-filter type microbial culture assays. Media in the outlet chamber feeds the trapped organisms in the filter element in a manner similar to that found for membrane filters incubated on media soaked pads.

The half-fill configuration provides several advantages over the previously described full-fill configuration. It allows the formation of colonies that can be counted in a conventional manner, preferably using chromogenic reporters to specifically identify organism types. The open inlet chamber provides better gas exchange than the fluid filled chamber and is more similar to a conventional membrane filter configuration, thereby making for similar test interpretations. Finally, although not unique to the Half-fill configuration, fluorescent reporters from the membrane bound organisms are readily observed both in the colonies and in the fluid filled outlet chamber making the half-fill configuration nearly as sensitive as the full-fill configuration.

EXAMPLES

Example 1

Sample Preparation, Assay and Organism Recovery Using the Integrated Bioassay Method A number of different form factors are included as examples of integrated filter Assay Cartridge devices (IFAC). Similarly, there are several methods that can be used to prepare samples for testing in the Integrated BioAssay (IBA). Perhaps the simplest IFAC example device is a syringe filter (e.g., Pall Acrodisc™) as shown in FIG. 1; typically a small round disk device with an inlet and outlet port which may have luer-lock fittings on one or both of the ports. A simple preparation method for these syringe filters useful for testing small sample volumes is to simply add the test volume and detection fluids using a pipettor. As a simple example of the syringe filter's utility as an IFAC, a dilution series of microbial samples (*E. coli*) was prepared using 13 mm Pall Acrodisc™ syringe filters and a pipettor then tested in the Rapid BioAnalyzer (RBA).

Serial dilutions of *E. coli* (ATCC 25922) were prepared in a phosphate buffered saline solution such that the highest dilutions contained 0-5 organisms. Using a pipettor (Gilson), 1 mL of each organism dilution was drawn up and dispensed through the syringe filter. By similar means, the samples were then washed with two 1 mL aliquots of the buffered saline solution after which 0.7 mL of growth media was added to the device, thereby flushing out all remaining rinse buffer. Prior to detaching the pipette tip from the IFAC, the outlet was plugged with Critoseal™ (a vinyl-plastic putty). A cap or handle was added to the filter disk to enable easier handling and protection from contamination during incubation. These samples were then placed in the RBA and the instrument and measured over a 10 hour period. The growth curves for these samples are shown in FIG. 6.

Figure 6:
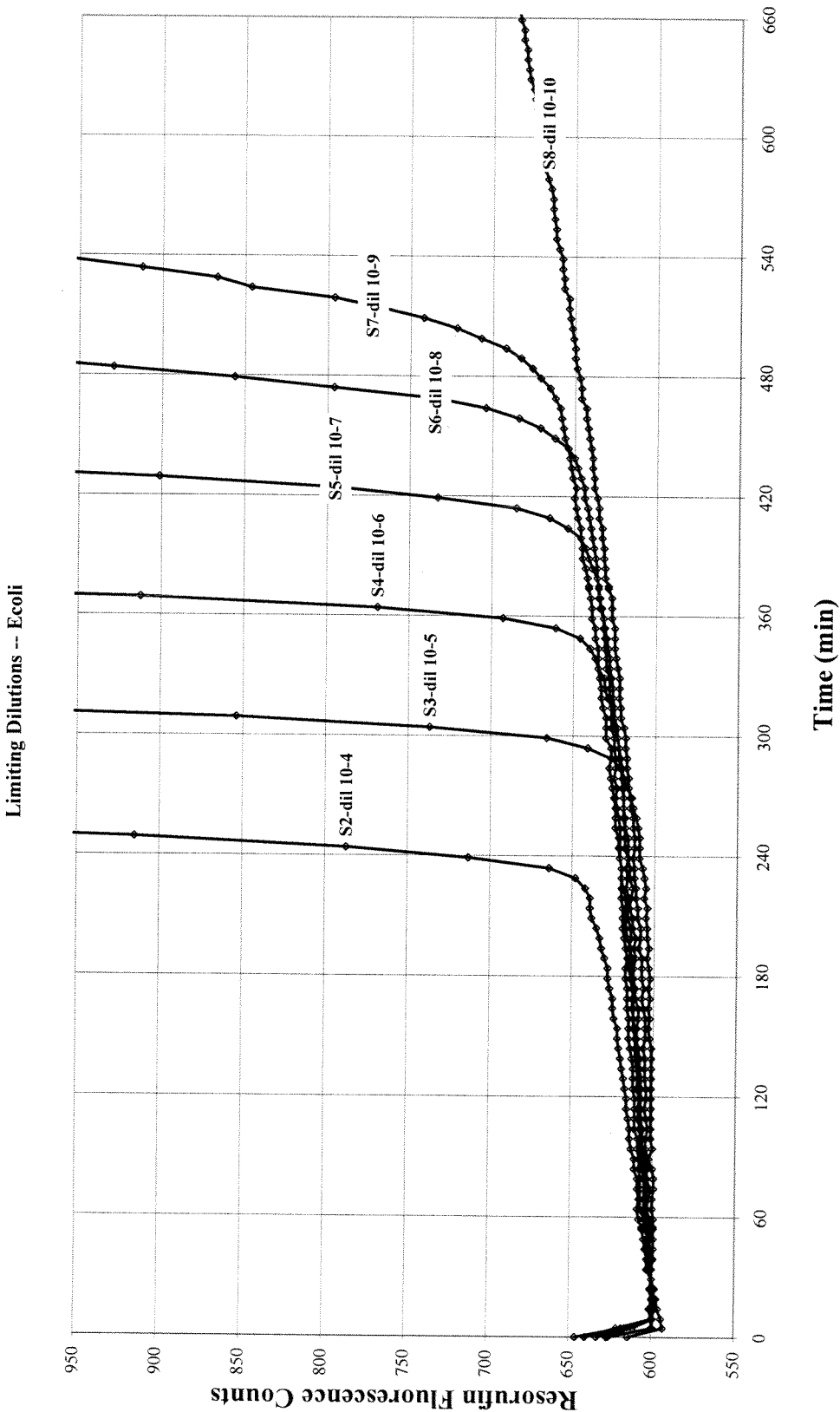
FIG. 6 provides growth curves for *E. coli* using resorufin-glucuronide as a fluorescent reporter for its growth. The time at which the signal rises above background is termed the Time to Detection (TTD) and is related to the number of organisms present in the sample at the start of the assay.

The data shown in FIG. 6, show the instrument's measured changes in one fluorescent signal (the resorufin reporter for E. coli indication) for each of the seven E. coli dilution samples as a function of the assay/incubation time (the highest dilution contained no cells thereby was equivalent to a negative control). The results indicate for the six different starting concentrations of E. coli that each has a "growth" curve exhibiting similar characteristics: there is an initial period with only linear change in the fluorescent reporter generated, followed by a period of rapid increases in the reporter signal development. The point at which this inflection change occurs is referred to as the Time to Detection (TTD).

The differences in TTD between samples are remarkably consistent and proportional to the number of organisms in the starting fluid sample and the type of organism present. Quantitation of the sample start number is accomplished using the simple equation previously described. Estimates of the Nega-Time and doubling time for E. coli and non-E. coli Total Coliforms use results generated from multiple series of experiments, such as outlined in this example, conducted on lab acquired (e.g., ATCC) and environmental sourced organisms in using the Integrated BioAssay system. Estimates of the SafetyTime were similarly made using environmentally sourced organisms.

Another important aspect of the Integrated BioAssay system's utility is its ability to recover similar numbers of organisms when compared to recognized standard methods. To address this aspect, 10 replicate samples of environmental water diluted to contain 0-5 organisms were prepared in either the IFAC as described above or in 12×75 mm glass tubes with standard EC-MUG (IDEXX) media. Negative control samples (sterile water) for each assay type were also prepared. These samples (10 replicate IFAC and 10 replicate tubes+controls) were incubated at 37° C. for 24 hours and visually assessed for the presence of the appropriate indicator (e.g., resorufin or 4-MU respectively).

Media in negative control samples prepared in either tubes or the IFAC remained straw colored indicating no growth. In contrast, four of ten tube samples turned yellow with white fluorescence indicating growth of E. coli. Similarly, five of ten IFACs turned red (red fluorescence) with white fluorescence indicating growth of E. coli.

The similar rates of positivity between the two sample preparations indicate that there is no difference in the sensitivity or recovery of the two methods, further demonstrating the utility of the Integrated BioAssay approach.

Example 2

Detection of Growth by the Integrated Bioassay—Utility of Derivative Calculations The following example is presented to illustrate the type of data that the instrument can acquire and that a single "assay endpoint" can easily lead to incorrect conclusions regarding the presence or absence of viable organisms in unknown environmental samples. Further, the example demonstrates the valuable utility of the derivative calculations used in the IBA approach to determine if and when growth of viable organisms has occurred.

The fluorescent signal in a test sample can change for several reasons unrelated to actual growth of the target organism. Hydrolysis of the glucuronide or galactopyranoside bond will occur at a slow but measurable rate, releasing the fluorescent reporter conjugates. Samples with glucuronidase or galactosidase enzymes present in samples at the initiation of the assay will contribute to changes in fluorescence. These enzymes can come from senescent target organisms, viable but not culturable (VBNC) organisms, or a number of gram positive or gram negative organisms that are otherwise inhibited by the media. The hydrolysis rate and production of fluorescent molecules can be highly variable, making it nearly impossible to define a single fluorescence signal threshold indicative of viable organisms. Similarly, the variable initial concentration of enzyme present in the system makes it nearly impossible to predict the presence, let alone the number, of viable target organisms.

Consequently, we have found that it is critical to identify growth by observing the time curve and identifying positive inflections in the time varying curve. This visual process has been systematized and automated by utilizing calculation of a $2^{nd}$ derivative of the signal (as a function of time) and determining if and when the $2^{nd}$ derivative crosses a critical threshold level. The following is a simple example demonstrating the utility of the $2^{nd}$ derivative.

Figure 7:
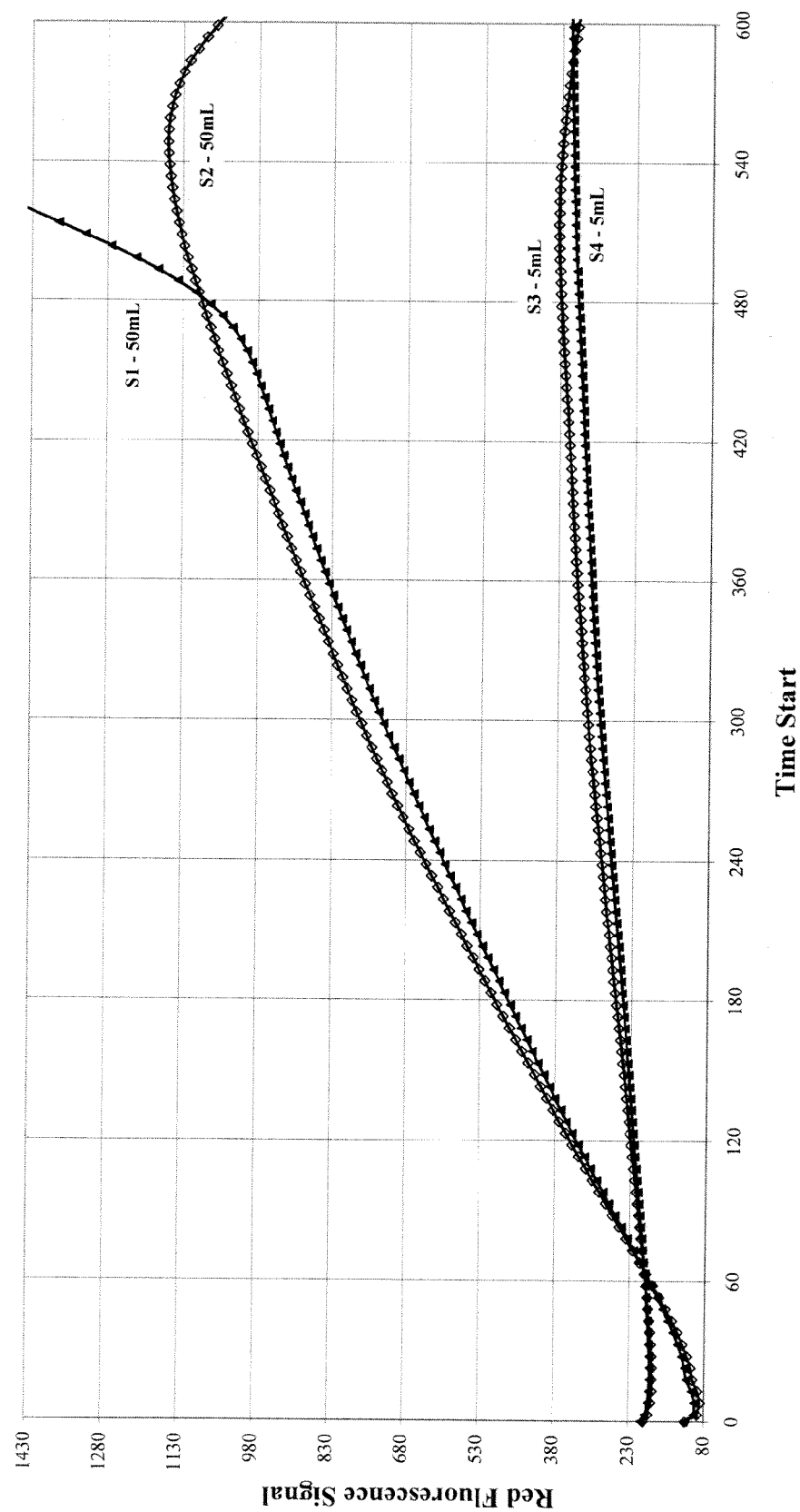
FIG. 7 is a graph showing fluorescent signals as a function of time from samples prepared with natural water sample sources with ≈1-7 *E. coli* and ≈7-15 nEcTC per 100 mL. Samples of 50 mL or 5 mL were flushed through an IFAC and developed with PacTec media in the BioAnalyzer. Although both 50 mL samples demonstrate rapidly increasing fluorescent signals, only one sample shows *E. coli* growth indicated by the upward inflection of the signal curve—its companion sample never developed a Resorufin signal. To automate growth detection, signal analysis must correctly differentiate production of fluor due to background enzyme activity versus active cellular growth.

Replicate samples were prepared in IFACs using two different volumes of water (5 mL and 50 mL) from a surface water source. Using standard methods (membrane filtration and plating with MI media—Whatman) to evaluate the number and type of organisms, the source water was shown to contain between 1 to 7 E. coli and 7 to 15 total coliforms in 100 mL. FIG. 7 shows the fluorescence-time curves for these replicate samples. The upward inflection shown in one of the 50 mL samples reliably indicated growth by viable organisms. In contrast, the other 50 mL sample while also having a rapidly rising signal that went to a high level, did not contain viable E. coli (that outcome being consistent with the very low concentration of culturable E. coli in the sample volume and the statistical probability of a given sample containing no organisms).

Figure 8:
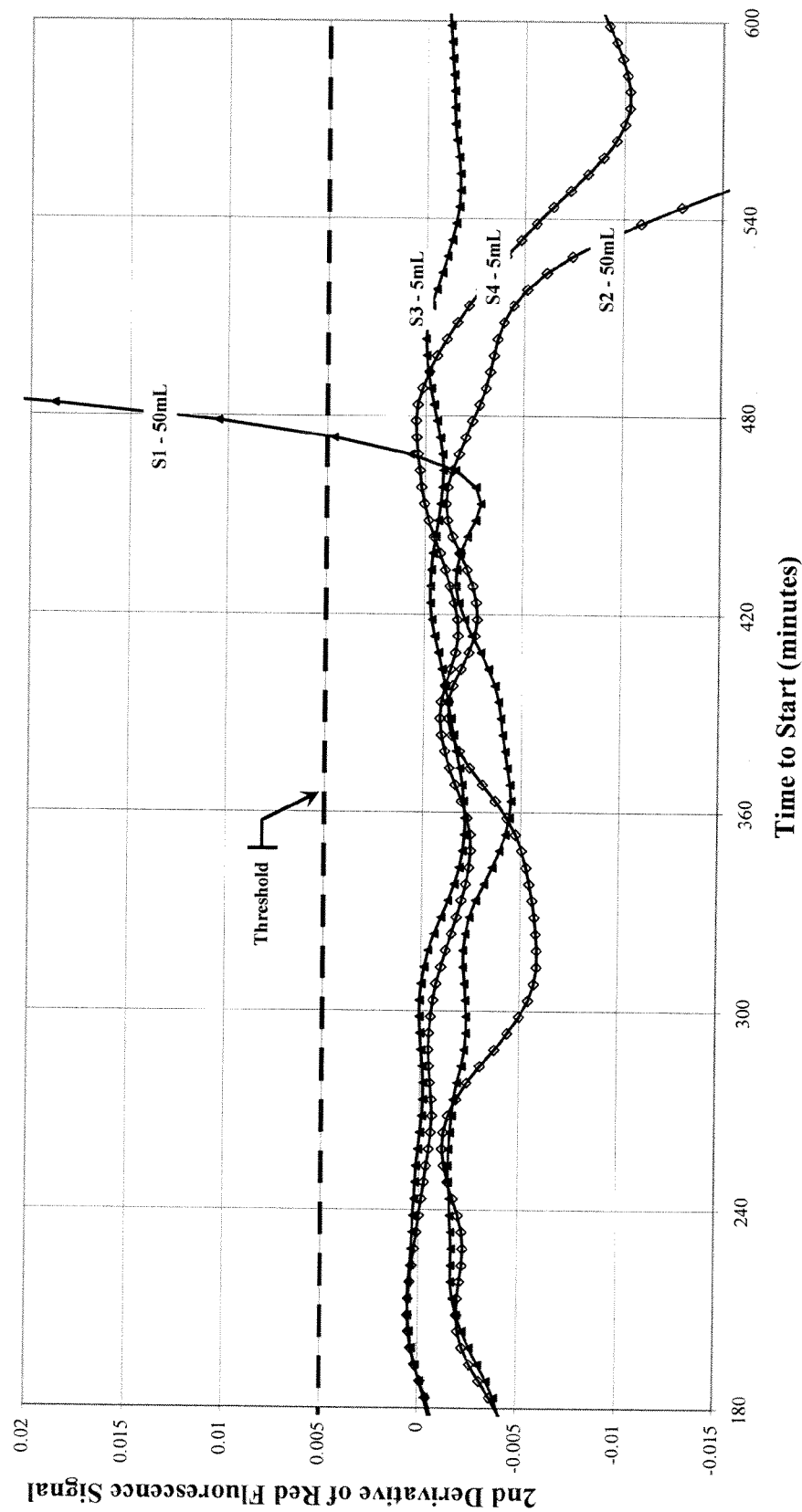
FIG. 8 is a graph which shows use of 2nd derivative for systematic isolation of optical signals indicating growth vs those due to background enzyme activity in non-viable or non-replicating cells. Signal data shown in FIG. 7 is transformed by calculating a 2nd derivative of the time varying data. The time point at which the 2nd derivative becomes greater than a threshold value is the Time To Detection and a robust indicator for the presence of viable organisms.

Instead, the preferred approach, which is a more reliable indication of true organism growth in a sample and avoids the shortcoming just described is the analysis of the time varying signal using a $2^{nd}$ derivative can accurately identify inflection points associated with growth. The data from FIG. 7 is recalculated using a $2^{nd}$ derivative analysis. As shown in FIG. 8, the signal derivative for the one positive sample (S1) is clearly differentiated from the other three negative samples (S2-S4). By measuring the time when the $2^{nd}$ derivative crosses a defined threshold, not only can the presence of a target organism be identified, a Time to Detection (TTD) is established. As noted in Example 1, the TTD is related to the number of viable organisms present at the start of the assay, providing a semi-quantitative estimate of the target organism concentration.

Example 3

Method for Sample Preparation in a Syringe Filter Using Negative Pressure

Water collected from a drinking water source was assessed for the presence of coliforms and E. coli in a simple, integrated manner using the integrated filter device (IFAC) and bioassay instrument. Compliance with regulatory statutes requires testing of 100 mL of water for the presence (or absence) of any coliform bacteria. The following example describes a simple method for preparation of the syringe version of the IFAC using negative pressure (suction) to process 100 mL samples. Additionally, the example provides a simple description of how the Integrated BioAssay can be used to assess toxicity of a water sample by measuring metabolic changes in a known organism. One-hundred milliliter samples are conveniently prepared and tested in the following manner.

Two 300 mL samples of tap water were collected into sterile glass bottles, one with 10 mg sodium-thiosulfate and one without thiosulfate. The water in each bottle was then spiked with sufficient E. coli (ATCC 25922) to give a final concentration of about 10 cfu per 100 mL. The samples were kept on ice for 45 minutes to simulate transport to a test lab, then processed. In this description, a syringe filter (e.g., a Pall Acrodisk™) was used as the integrated filter assay device (IFAC). A large 100 cc syringe barrel was attached to the inlet port of the syringe filter and the outlet port was attached to a vacuum source. The syringe barrel was filled with 100 mL of sample water and a vacuum applied to the IFAC outlet until only ≈1-2 mL of water remained in the syringe barrel. Fifty-milliliters of a phosphate buffered rinse solution (EPA dilution buffer) was added to the syringe barrel and then suctioned through the filter; stopping the vacuum when the wash solution was at or near the neck of the syringe. A small aliquot of growth media (1 mL) was added to the syringe and suctioned through the Acrodisc whose outlet was then sealed with a plug of Critoseal. A sterile pipet tip was inserted into the inlet port to act as a protective vent and handle.

Figure 9:
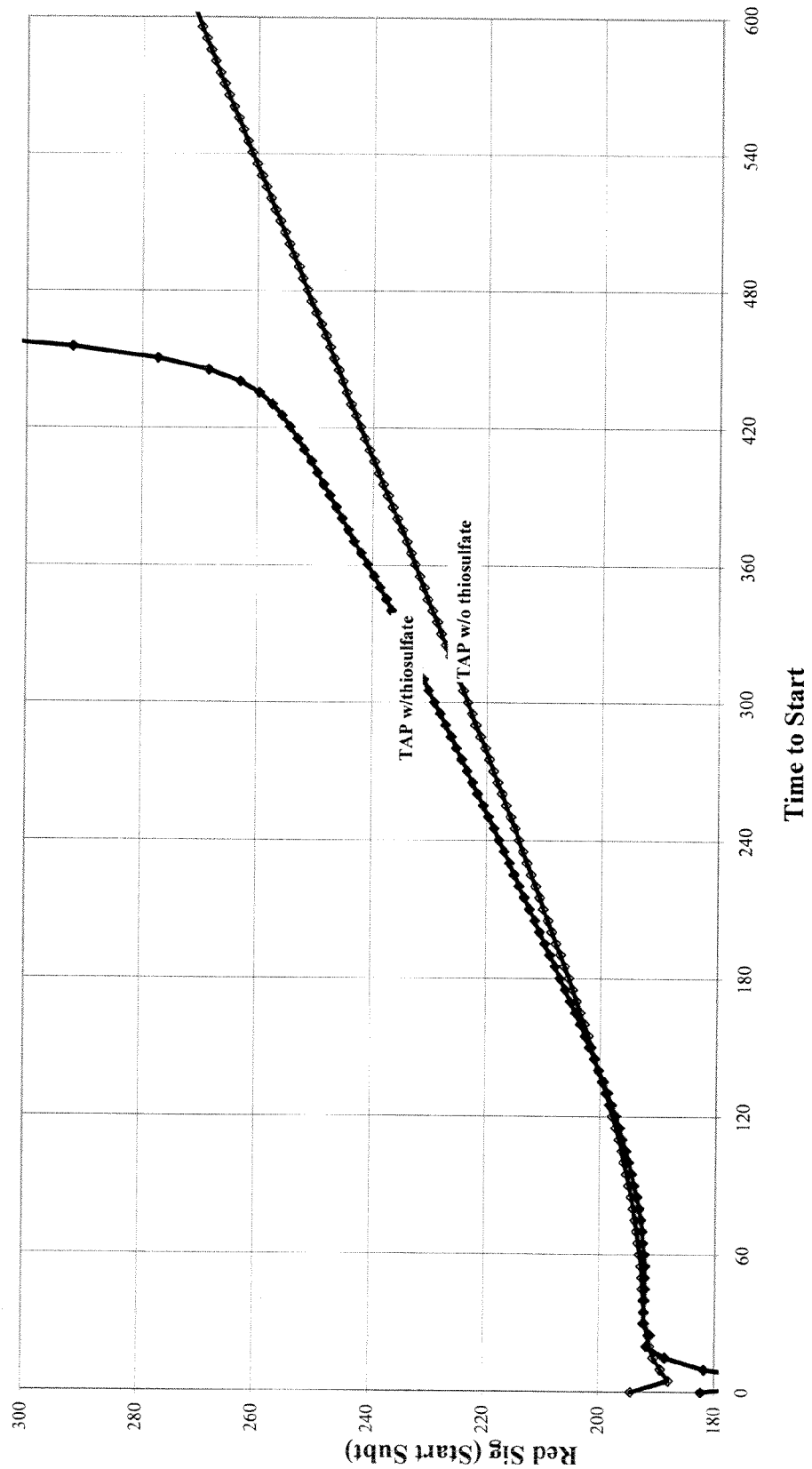
FIG. 9 is a graph showing *E. coli* specific fluorescence signals (resorufin-glucuronide) for tap water spiked with *E. coli*.

Samples from both the thiosulfate treated and untreated waters were prepared in the above manner. In addition, water was assessed using standard membrane filtration methods, as described in Standard Methods for Water & Wastewater Analysis. The IBA results are shown in FIG. 9. The results from both the IBA and the conventional membrane filtration were congruent. Namely, the spiked E. coli only survived in the thiosulfate treated water, and were presumably killed in the untreated water containing chlorine residuals (which the thiosulfate neutralizes).

Closer consideration of the IBA data reinforces the need to utilize a derivative based analysis of the fluorescence curves. Both the treated and untreated samples showed a remarkably similar fluorescent reporter signal increase over the first 400 minutes of the assay suggesting that although chlorination will inactivate a cell's ability to proliferate, it may not destroy some of the enzyme systems in the cell. This illustrates the need for enzymatic evaluations of water from, for instance a treatment plant, to utilize a means for viability assessment as opposed to simply measuring a final fluorescence level.

Finally, it can be appreciated by those practiced in the art of biological assays and toxicity assessments, that metabolic and viability assessments of a known organism spiked into a sample can be conducted in the IBA system to determine the toxicity of the test matrix (e.g. chlorinated water). The system clearly has the ability to distinguish cell viability after treatment with the chlorinated water. Careful examination of the difference in signal production noted between 180 to 400 minutes is indicative of a decrease in enzymatic activity of the treated sample. It can be further appreciated that the system's sensitivity could be used to analyze a dilution series to demonstrate small differences between treatments (e.g., amount or exposure time of chlorine).

Example 4

Preparation of Samples Using µIV Filters and IBA Estimation of Coliform Concentration for a Surface Water Sample The µIV filter is a preferred device for large volume sample preparations—especially highly contaminated surface water samples (e.g., rivers, lakes or reservoirs). The hydrophobic vent can be useful in prevention of airlocks during sample preparation and can be of further value in providing improved gas exchange as the sample grows. A typical micro-IV (µIV) filter is shown in FIG. 2. Additionally, a 14 g vinyl tube attached to the inlet port is used for insertion into and collection of the sample. A tube attached to the outlet port is then attached to a vacuum source to allow drawing up a sample through the device. Organisms from the sample are trapped on the filter which is then conveniently processed by further washing and addition of growth media to the fluid chambers. The following example describes collection of a water sample into a µIV filter in the field for later testing in the Rapid BioAnalyzer (RBA).

Samples of beach water were collected in a 300 mL polypropylene wide-mouth bottle. The IFACs were prepared using a Pall pediatric-IV filter with a 3" tube (14 g PVC) attached to the inlet port of the filter and a 100 mL, 10 mL or 1 mL syringe was attached to the outlet port via a non-collapsible Tygon™ tube. The inlet tube of the IFAC was inserted below the surface of the water and 100 mL, 10 mL, 1 mL or 0.1 mL of sample water were drawn through replicate filters. The syringe was detached, evacuated then reattached to the Tygon™ tube and ≈5 mL of EPA rinse buffer was drawn through the IFAC. Finally, growth media containing Resorufin-glucuronide and Ethyl-hydroxy-courmarin-glalctopyranoside (RES-glu & EHC-gal respectively) was drawn into the device. The inlet tubing was removed and the port plugged with Critoseal™ and the outlet tube replaced with a sterile vented cap. These samples were then inserted into the RBA for continuous evaluation over a 10 hour period.

Conventional membrane filtration samples were prepared using 1:10 dilutions of sample water (i.e., 10 mL of 1:10 dilution=>1 mL of undiluted water), all drawn from the 300 mL sample. Membrane filters were incubated at 37° C. on a commercial selection/indication media (Colorex™, ECC media, PML Biological) for evaluation after 18-24 hours.

Using the equation shown in Example 1, the starting number of E. coli was estimated from the TTDs measured by the Rapid BioAnalyzer. The estimated E. coli concentrations, shown in the table below, were closely proportional to the dilution factor of the sample. More importantly, although slightly higher than the membrane filter plate count, the concentrations of E. coli estimated by the two methods were remarkably similar. Because the non-E. coli Total Coliform (nEcTC) counts were not a factor of 10 greater than the E. coli counts, the IBA system was not able to identify an excess EHC signal attributable to the nEcTC population.

|  | Organism | 100 mL | 10 mL | 1 mL | 0.1 mL |
|---|---|---|---|---|---|
| Integrated Filter Assay | Ecoli | 1018 | 108 | 9 | 1*/0 |
|  | TColiform |  |  | n/a |  |
| Colorex Plate | Ecoli |  |  | 24 | 1/0 |
|  | TColiform |  |  | 74 | 5/2 |

*one sample negative

This example demonstrates another of the IBA system's advantages—namely, the ability to measure samples over a wide range of starting organism number without a requirement for sample dilution. Additionally, the proportionality of the dilution factor and the TTD estimated *E. coli* further suggests that this procedure minimizes the risk of organisms adhering to the sidewalls of a filter funnel.

Example 5

Preparation and Interpretation of the μIV Half-Fill Configuration

The conventional medical usage of IV-filters is to fill both the inlet and outlet chambers of the device with fluid and push fluid through the device under positive pressure (pump or gravity). In the tests described to this point, after filtering the sample, both chambers of the IFAC were filled with media then incubated to develop color/fluorescence in both chambers of the device. In a significant departure from this method, an alternate configuration leaves the inlet chamber empty (air filled) with media in the outlet chamber bathing the membrane filter from the "backside" in a manner similar to conventional membrane filtration and subsequent culture on sorbent pads filled with media. The Half-fill configuration is easily achieved as described in the detailed description of the invention above. Briefly, after filling the IFACs with media, the inlet tube is removed from its source of media and suction is continued on the outlet port until all media is removed from the inlet chamber. Because the hydrophilic membrane filter, once filled with liquid will not pass air, the flow of liquid stops once the inlet chamber is emptied of fluid, leaving the outlet chamber filled with fluid. The outlet port is then plugged with Critoseal™ which serves to hydraulically keep the media held in the outlet chamber, preventing flow of media back into the inlet chamber. These half-fill configuration samples are tested in the RBA in the standard manner described previously.

Tests of the half-fill and full-fill configured IFACs show remarkably similar signal kinetics with typical differences in TTDs of less than 15 minutes—close to the TTD limit for identically prepared samples (i.e., all full-fill or all half-fill). There are, however, differences in the kinetics of signal development typically 100-200 minutes after the detection time has passed that indicates the two configurations are not identical. In a related manner, we have observed fluorescent signal shifts consistent with acid production by coliforms—typically a reduction in the fluorescent signal of resorufin or 4-MU. When the half-fill configuration is used, this pH shift is moderated, indicating that a volatile acid (possibly $CO_2$) is being better exchanged with ambient air in the half-fill configuration.

This observation of better gas exchange is further confirmed through observations of the oxygen-sensor signal development with OxIFAC used in the half-fill versus full-fill configuration. As will be shown later, changes to the oxygen concentration inside a full-fill OxIFAC provide an early indication of cellular metabolism and growth, similar to the fluorescent-conjugate reporters. In contrast, the half-fill configuration shows a damped oxygen response, suggesting that the gas in the inlet chamber is being exchanged (not unexpectedly) with ambient air through the hydrophobic vent.

Figure 10:
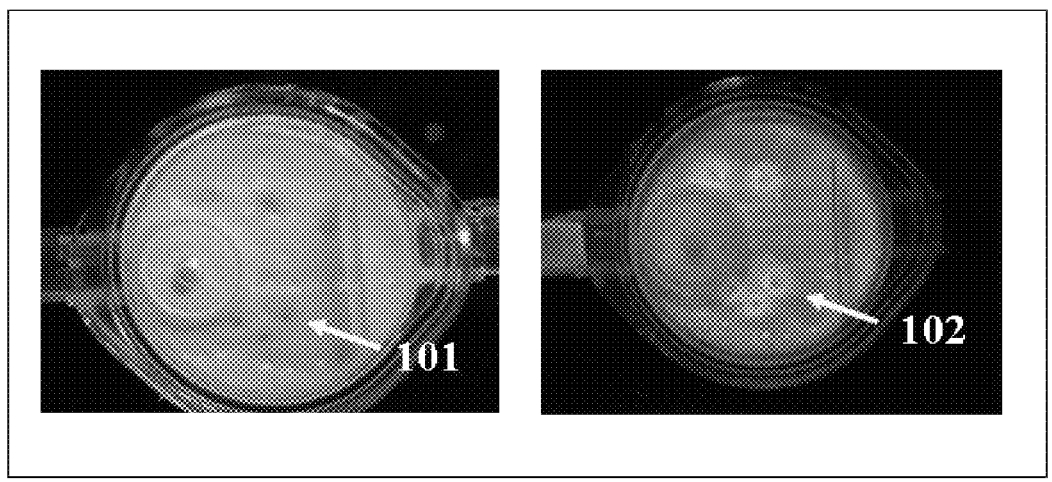
FIG. 10 provides photographs showing the development of colonies in half-fill configuration. *Klebsiella pneumoniae* added to sample water and developed with media containing X-gal (chromogenic) and EHC-gal (fluorescent). IFAC on left shows X-gal colonies (101) observed under visible light. IFAC shown on right is same device illuminated with UV blacklight and respective colonies (102).

The highly useful utility for the half-fill configuration is that it enables visual observation of filters to identify colonies growing on the surface of the filter membrane, inlet chamber side, typically 5-10 hours after completing the fluorescence signal analysis in the RBA. In our preferred assay procedure, both a fluorescent and a chromogenic reporter are added to the media. This allows for both instrumented fluorescent optical measurement of organism growth and visual observation of the IFAC results. FIG. 10 shows an IFAC with *Klebsiella pneumoniae* (ATCC 31488) growing on its filter membrane surface. In this example, the media contains the chromogenic X-galactopyranoside and fluorogenic EHC-galactopyranoside reporters. The *Klebsiella* organisms form distinct blue colonies under visible light and coincident white fluorescent colonies under UV illumination.

In a surprising result, we found that the substituted indoxyl chromogenic reporters demonstrate a distinct white fluorescence of their own. Literature states that the indolyl of these reporters is rapidly oxidized to form a non-soluble colored product. Assays utilizing 6-chloro-3-indoxyl-galactopyranoside (salmon-gal) demonstrate early colony formation with a bright white fluorescent center. As the colony ages and grows larger, a distinct white fluorescent halo surrounding a reddish colored center is observed. Similar dual fluorogenic/chromogenic results have been observed for other substituted indoxyls with the exception of 5-bromo-4-chloro-indoxyl-conjugates (e.g. X-gal or X-glu) which demonstrate only minimal fluorescence.

Figure 11:
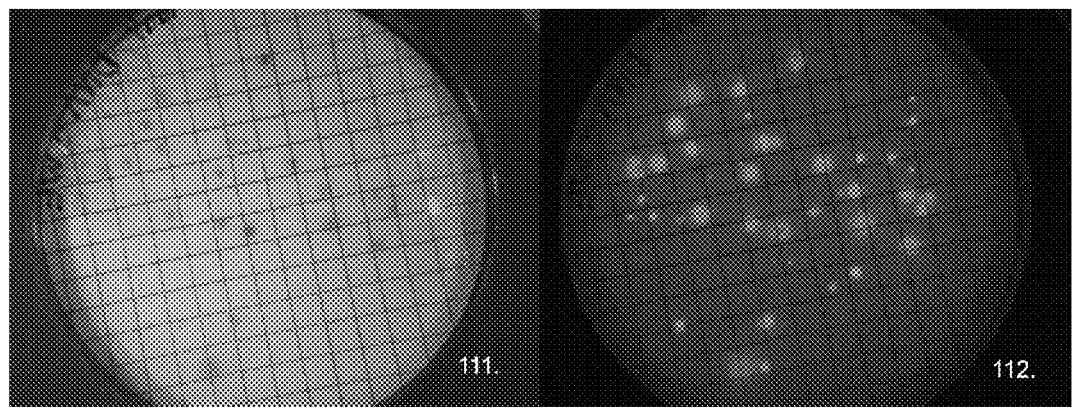
FIG. 11 provides photographs showing an environmentally derived sample grown on a membrane filter for 15 hours using media with X-glucuronide and Salmon-galactopyranoside as reporters. Visible color development shown in panel 111 is difficult to discern in many colonies. Fluorescent light development shown in panel 112 is readily observed with all fluorescent colonies developing distinct visible red color by 24-26 hours.

An environmentally derived sample was filtered and grown on a membrane filter prepared using 6-chloro-3-indoxyl-galactopyranoside (salmon-gal) and 5-bromo-4-chloro-indoxyl-glucuronide (X-gluc) in the growth medium. FIG. 11 shows the membrane filter observed using either visible white light or under UV light. *E coli* are typically distinguished as colonies with a dark purple coloration under white light. Additionally, we find that as a result of the salmon-gal conversion, *E. coli* and Total Coliforms demonstrate a distinctive white halo when viewed with a UV-light. Eventually with continued incubation, the white halo will disappear, leaving only a red or dark purple color for Total Coliforms or *E. coli* respectively. At earlier times however (14-18 hours), the presence of a halo in light blue/teal colony can be used to identify organisms with expressing galactosidase and glucuronidase (i.e., *E. coli*) from organisms with only glucuronidase (non-*E. coli*). Similarly, the white fluorescence of the salmon-gal can be used to identify Total Coliforms (gal-positive organisms) before they are clearly identifiable by visual color.

Example 6

Post Processing Analysis of the IFAC

A key advantage of the IFAC approach is the ability to easily and completely flush a test media from the inlet and outlet chamber and replace the media with a second media (e.g., a confirmatory media) or a developing reagent.

We have found particular utility in measuring the indole response of IFAC sample cultures after overnight incubation and measurement in the RBA. Indole production is characteristic of *E. coli* and is used as a confirmation tests used to identify *E. coli* presence. The indole confirmatory test is performed using either the full-fill or the half-fill IFAC configurations in the following manner. The Critoseal plug is removed from the IFAC inlet port and the inlet chamber gently rinsed with phosphate buffered saline then gently flooded with Kovac's reagent and allowed to stand for 5-15 minutes. The appearance of a red coloration in the solution is indicative of the presence of *E. coli*. In the IFAC half-filled configuration individual colonies displaying a red color are readily identified.

Those practiced in the art will recognize that the second reagent could be chosen from any standard confirmatory chemical normally used on a microbiological growth plate. Similarly, a second growth-indicator media could be flushed through the IFAC and reading with incubation continued to look for the development of different reporters or the enhancement of the initial reporter/indicator molecules.

Preferably the IFAC is made with its parts and chambers separable, such that coverings of the inlet chamber or the outlet chamber are removable allowing access to the contents of the IFAC in order to perform assay-procedural operations or the post-processing being described. It is possible to physically remove the plastic forming the cover to the inlet chamber of existing conventional filtration devices of the types useful as IFACs as described herein. Two methods have been successfully used. The first takes advantage of the typical manufacturing method used to form the μIV filters, namely that the filter device consists of two fitted pieces that form two chambers with a filter membrane welded typically to the outlet chamber piece. For some manufacturer's parts, the inlet cover can be pried off the base, exposing the membrane filter. Alternatively, a hot-knife can be used to cut the inlet chamber piece off of the device, thereby exposing the filter membrane. Cutting jigs for this latter approach can be made that allow for rapid and effective exposure of the filter membrane. After exposure of the filter membrane, standard microbiological or molecular tests can be conducted on either colonies picked from the membrane surface or small sections of the filter excised for further analysis (e.g., DNA probe testing).

Example 7

Alternative Reporters—Oxygen and pH

In addition to using the enzyme specific chromogenic and fluorogenic reporters detailed in the above examples, general reporters can be used to detect the presence of viable organisms and measure their growth or metabolic activity in the IFAC. In particular, we have found that the oxygen-sensitive IFAC (OxIFAC) described above can be very useful for testing the effects of various treatment conditions on a population of cells, and especially for comparing effects of different exposure conditions in one OxIFAC sample versus another. For example, we have used the OxIFAC to differentiate the growth potential of different media on different populations of cells (e.g., TSB versus MI broth, Coliscan MF, and the PacTec media formulation presented above). Alternatively, in a different type of application, assays with OxIFAC have been used for comparing the effect of different media on one cell type in order to differentiate the type of cell being analyzed (e.g., a contaminate of a bottled water sample comparatively assayed on TSB versus PacTec media, which served to confirm that the contaminate was not a Coliform as it did not grow in our selective media, but it did in the nonselective TSB media). Similarly, use of a fluorescent pH indicator either in the detection fluid or affixed to the internal aspects of the IFAC usefully serve to detect pH changes in the fluid volume which thereby indicated changes associated with biological activity.

Oxygen Studies

Several tests were conducted with $E.$ $coli$ (ATCC 25922) using the oxygen sensitive IFACs described previously (OxIFAC). The analyzer instrument was set up to run in phosphorescence mode, measuring the luminescent decay during two periods after the LEDs had been turned off. The signal ratio of these two periods was used to calculate a luminescent lifetime surrogate measure and this lifetime measure was compared to a fluorescence measure using the fluorescent conjugate reporters Resorufin-glucuronide and EHC-galactopyranoside. A water sample containing approximately 50 freshly harvested $E.$ $coli$ was added to replicate OxIFAC's or standard IFACs. The filters were then filled with the PacTec fluorescent growth media and measured in the RBA luminiscence reader.

Figure 12:
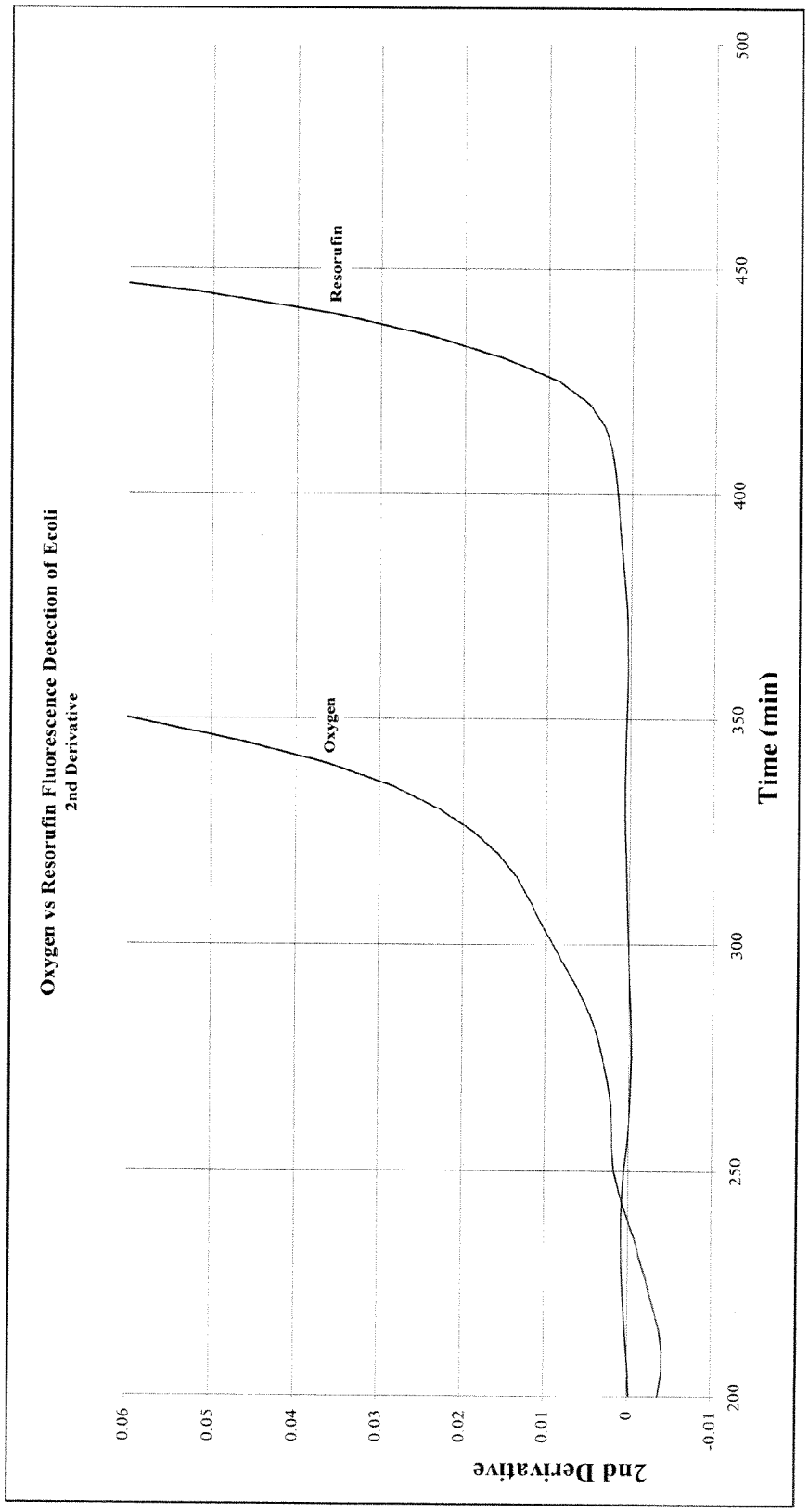
FIG. 12 is a graph of Oxygen Phosphorescence versus Resorufin Fluorescence Detection of 50 *E. coli*—TTD's for the oxygen method are about 100 minutes faster than those for fluorescence.

As shown in FIG. 12, we found that the oxygen-based metabolic assay showed growth curves similar in nature to those in the fluorescent assay, but with significantly temporal differences. The OxIFAC oxygen measurement was able to indicate growth about 100 minutes earlier than the Resorufin fluorescent-substrate reporter. Comparison with the EHC fluorescence reporter showed an even larger difference in detection times (data not shown).

Figure 13:
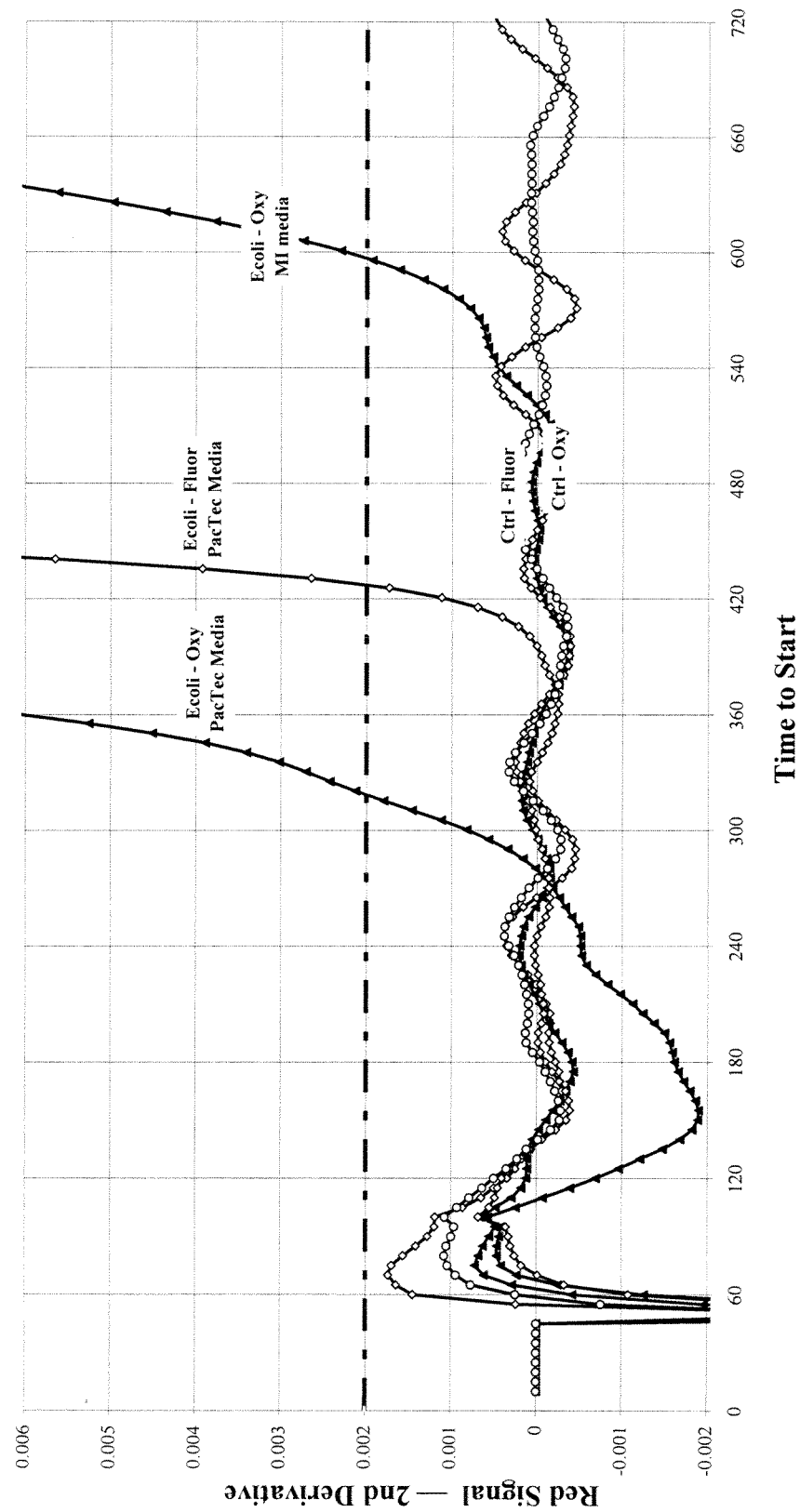
FIG. 13 is a graph showing results of a test indicating the utility of the oxygen measurement to compare growth of stressed *E. coli* in PacTec versus MI media. The oxygen and fluorescence response for 10 *E. coli* in fluid with greater than 10$^3$ excess non-viable stressed population. The PacTec media was shown to be significantly faster than the MI media in detection of stressed population.
Figure 14:
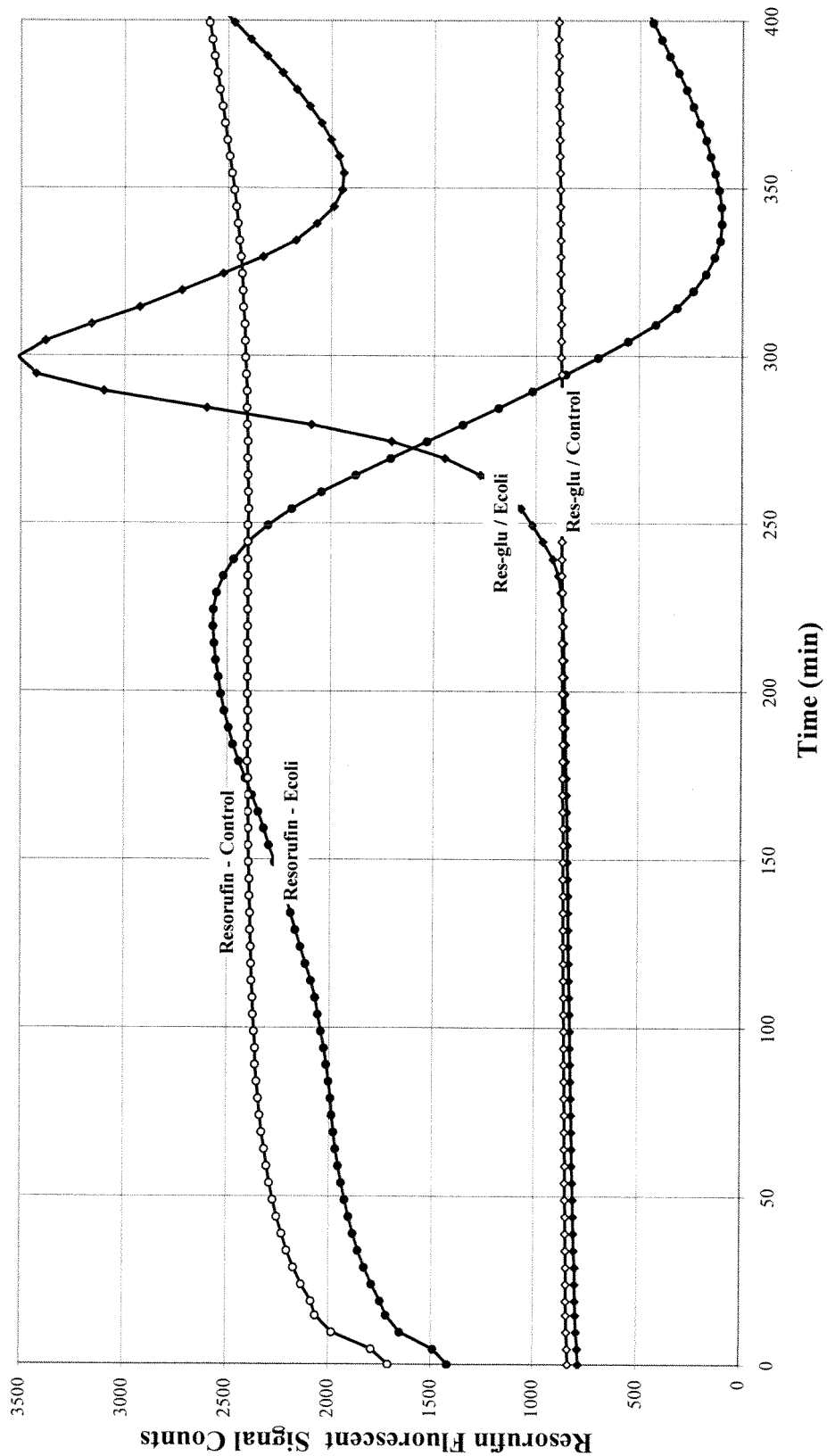
FIG. 14 is a graph showing pH changes occurring in an IFAC during growth of *E. coli*. The fluorescence signal of an IFAC prepared with a pH indicating fluorophore (resorufin) only is compared with an IFAC prepared with a resorufin-glucuronide conjugate. After an initial upward pH shift observed in both control and *E. coli* spiked samples, the pH rapidly drops coincidentally with the initial detection of *E. coli* replication.
Figure 15:
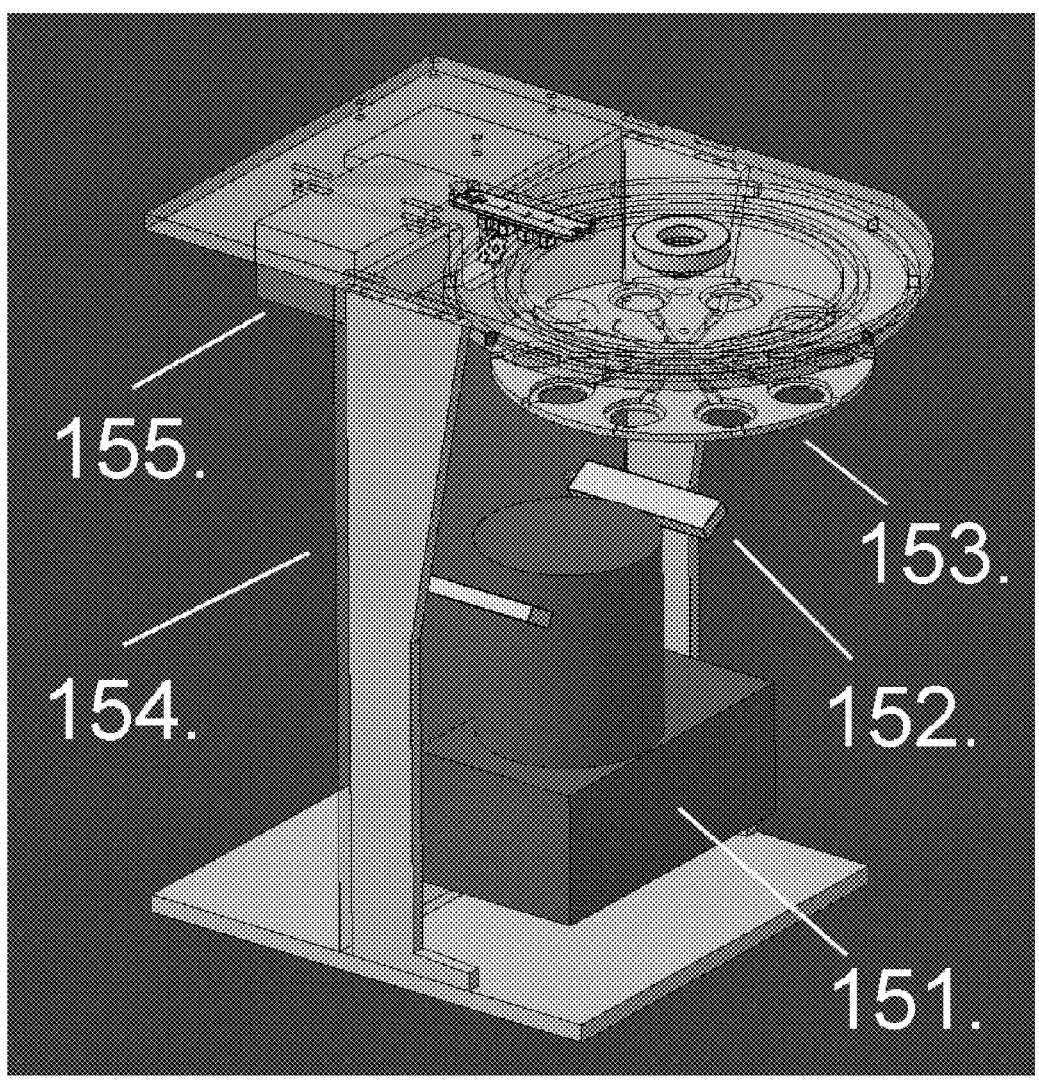
FIG. 15 is an alternate embodiment of the Rapid BioAnalyzer instrument. The figure shows a charge coupled device imaging sensor camera (151) attached to instrument frame (154). Motor (155) turns and positions rotary stage (153) for holding filter cartridges which are illuminated by LED bar (152).
Figure 16:
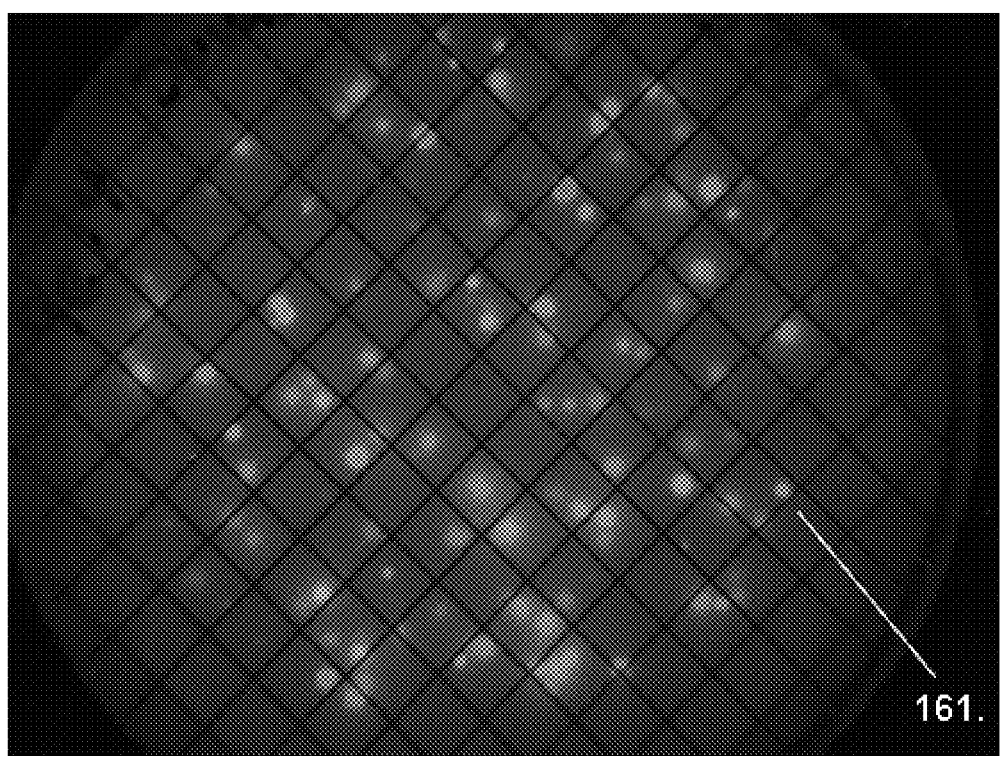
FIG. 16 is an example of captured picture from imaging device showing: colony dispersion uniformity, diversity, colony intensity, separation, and signal contrast of exemplary colony (161).

A similar study was conducted using $E.$ $coli$ (ATCC 25922) held in water for approximately 2 months. In this solution of water-stressed organisms, the number of "non-viable" organisms in the solution was approximately 1000× greater than the number of "viable" organisms. Replicate samples containing approximately 10 viable $E.$ $coli$ (as measured on a Tryptic Soy Agar plate) were added as spike "challenges" to both standard IFACs or to OxIFACs then filled with either PacTec growth media or a commercial preparation of MI media (Whatman). The samples were measured in the RBA using the fluorescence or phosphorescence mode as described previously. We discovered that the large number of dead organisms contained in the spike solution provided enough glucuronidase and galactosidase enzymes to engender a large background conversion of the fluorescent-conjugate reporters in both media as assayed in the RBA. Consequently, analysis of the fluorescence signal used the second derivative in order to determine the TTD's. An identical $2^{nd}$ derivative analysis of the oxygen signal response was also performed and the results are summarized in FIG. 13.

Again, the oxygen response was observed to be about 100 minutes faster than the fluorescent (Resorufin) response. A particularly striking finding was the difference in detection time (TTD) between the PacTec media and the MI media. Using the generalized oxygen sensor response, a clear difference in the growth promotion between the two media was demonstrated.

Although a nonspecific oxygen bioassay is generally much faster than the specific substrate-reporter method, because differentiation of $E.$ $coli$ and non-$E.$ $coli$ Total Coliforms (nEcTC) is a primary requirement for testing drinking and surface water quality, the fluorescent substrate-reporter methods described earlier in this report remains the preferred detection means for coliform bioassays.

Nonetheless, the OxIFAC oxygen assay can be gainfully employed towards such as the water-quality testing, alone as an adjunct to the main fluorescent test. For instance, the oxygen bioassay will provide an earlier warning indication that some viable contaminant organism is growing in the OxIFAC sample. However, if there is no early pre-indication of a contaminant, then no reason to expect for instance in the water-quality test that subsequent incubation and analysis with yield an indication of an $E.$ $coli$ or coliform. Thus we might significantly reduce the assay time needed to derive a conclusion that a sample is negative and that the water is clean and safe. Analogously, for those fluid samples that should be clean, or sterile, devoid of viable organisms, this early indication by the OxIFAC oxygen assay whether the sample does or does not have contaminants constitutes by itself a valuable test, regardless of the type of contaminant(s) present.

pH Studies

As indicated, pH changes and the use of pH indicators are applicable as useful indictor-means and approaches to RBA analyses with the inventive methods and devices. For example, previously referenced reporter, resorufin, is a fluorescent molecule that, like most fluorescent molecules, demonstrates pH sensitivity. Most notably, as the pH decreases, the fluorescence yield of the molecule decreases and therefore the fluorescent signal decreases as well. Consequently, for bioassays utilizing, for instance, a single point static measure of 4-methyl umbelliferone fluorescence, the solution pH is alkalinized by the addition of NaOH to make the measurement conditions consistent and to enable comparisons between samples.

As a study of the pH conditions in an IFAC syringe filter during a bioassay, which illustrates the capacity of using pH measurements as the basis of IBA assays, a media was prepared with free resorufin (50 µg/mL) but without any fluorescent-conjugate reporters (e.g., resorufin-glucuronide). An IBA bioassay was setup with either E. coli or phosphate buffered saline added to the IFAC followed by either the standard indicator media with resorufin-glucuronide describe previously, or the resorufin-only media. The IBA test results demonstrated that, based on the resorufin-only sample, the pH in the filter cartridge exhibits a measurable change, beginning to decrease at approximately the same time point as resorufin production becomes measurable in the other sample with resorufin-glucuronide. Moreover, the pH continues to decrease for about 100 minutes. It is noteworthy that in this context of pH measures and sensitivity of resorufin to pH, that in the example presented there is a downturn seen at 300 minutes into assay of the resorufin-glucuronide sample signal with E. coli present. This is due to the free resorufin reporter that ultimately appears in the sample, generated by the E. coli activity, revealing that the pH in the sample is falling and causing a reduction in fluorescence, in the same manner as reflected by the resorufin-only sample. The pH decline in these samples is consistent with the activity of E. coli, whose known production of acid is used as one indicator or identifier of the organism.

It can be readily recognized that pH indicators other than resorufin could be employed in the design of IBA assays. Selection of molecules with different pK's allows analyses over different pH regions and with different expected pH changes, such as a characteristic increase rather than decrease in pH.

Example 8

Non-Coliform Testing—Biological Indicators

In addition to using the IBA system for detecting the presence or measuring the activity of an entity in a sample fluid, it has great potential in developing assays employing biological indicators of environmental conditions. In this mode of application, a biological-indicator, for instance an organism, is introduced into the IFAC with the objective of measuring its response to an agent or condition that it is exposed to. This type assay approach is useful to conduct tests for indications of exposure to toxic or inhibitory conditions, or alternatively stimulatory or growth promoting conditions. In particular, the response of an organism with well established sensitivities can be measured before and after exposure to a test environment and its response used to judge the effectiveness of that environment.

Diverse examples include steam sterilization biological indicators and uptake and conversion of 4MU-galactopyranoside by Daphnia magna. For instance, Bacillus stearothermophilus spores applied to an IFAC are useful as an indicator to verify that subsequent exposure of the IFAC spore-challenged device to a steam-sterilization cycle has been effective in killing all of the spores contained therein (see further exemplary description below). Indicator organisms Daphnia magna and Artemia are useful indicators to show that their exposure in an IFAC to a fluid containing a toxic agent correspondingly results in reduction of their metabolic activity.

The IBA system can be used to measure changes in production of fluorescent reporters (as indicated in Example 1 above) or the oxygen and pH indicator versions of the system can be used as general indicators of metabolism. In the case of Example 1, using fluorescent reporters, it was demonstrated that differences between samples of E. coli prepared at different concentrations (dilutions) exhibited differences in their outgrowth characteristics and TTD as measured by IBA testing. It also serves an example of relevance to the utility of a biological-indicator test. Had the samples all been prepared with the same number of E. coli in the IFAC at the onset, to use the E. coli as biological indicators, with the organisms subsequently exposed to test solutions containing increasing amounts of an agent constituting a toxic substance that killed or inhibited outgrowth, then the IBA results would show a similar outcome. The more toxin present, the greater the inhibition/death, the fewer the cells present to produce a response, and the longer the TTD. Thereby, the test, with comparisons made between biological-indicator samples, serves to illustrate that it is both a means to identify the presence of a toxic compound and to titrate the concentration of the toxic.

Example 3 can also be regarded as exemplary of a biological-indicator based assay conducted with the IBA using fluorescent reporters. In that case IFAC were spiked with E. coli (the biological indicator) and one was exposed to a tap water containing chlorine while the comparator was not, the chlorine neutralized by thiosulfate treatment. The untreated sample with chlorine present indicated the growth suppressive effect of the chlorine, constituting a test of inhibition/toxicity of the sample fluid.

As relevant extensions of the above examples, the biological-indicator is not necessarily limited to being a known defined entity of specific identity. For instance, it could be a contaminant or infectious agent of unknown type whose antibiotic sensitivity and resistance needs to be established. By distributing and seeding samples of the organism between a number of IFAC and performing an IBA with each exposed to media containing different antibiotics, those treatment conditions exhibiting sensitivity or inhibition or growth can be differentiated from those that do not, i.e., the biological-indicator is resistant.

It can be similarly appreciated that in contrast to the use of biological-indicator model assays for measuring inhibitory effects using the IBA system, the test design can be aimed at identifying and quantitatively assessing stimulatory conditions in the assay environment. In such cases, the outcome using Example 1 again for reference, is an earlier TTD, as a result of more stimulation, induction, or growth promotion of the biological indicator acted upon by the stimulant.

The OxIFAC approach is useful for testing a variety of organisms where there is not a generally recognized enzyme reporter, or where pure populations of organisms are assayed. For example, steam sterilization biological indicators utilize pure populations of Bacillus stearothermophilus spores as an indicator of steam sterilizer efficacy. Our studies conducted with these spores in an oxygen-assay format have shown detection of 1-10 viable spores after sterilization within 8 hours compared to the standard 24 hours of incubation required. In failed sterilization runs with $10^3$ or more viable spores, detection times can be as fast as 45 minutes. It can be readily appreciated that this approach could be similarly applied to other biological indicators (e.g., B. subtilus) and other sterilization conditions to rapidly determine the efficacy or a treatment (e.g., EtO sterilizations in the medical industry, or hydrogen-peroxide vapor phase decontamination of rooms and buildings).

It can also be readily appreciated that the oxygen-assay mode is applicable to measuring relative differences in test environments as well (as shown in Example 7). In addition to measuring differences in the TTD for various additives or pre-treatments, the differences in reporter production can be used to define more subtle effects on enzyme systems that are not readily measured by cell division.

One example that takes particular advantage of the IFAC's ability to easily and reproducibly sample large volumes of water includes industrial cooling towers. These structures are prone to development of biofilms that reduce heat exchange efficiency and can lead to increased corrosion rates. The addition of excessive microbial-control agents is undesirable due to environmental impacts as well as cost. Replicate samples of the cooling water and its resident organisms are easily prepared by filtration and harvesting in the IFAC or OxIFAC. Various antimicrobial treatment agents and agent concentrations are then testable in either of two manners: (i) by inclusion of the agent in the culture media this is administered to the assay devices, with subsequent incubation and analysis by the IBA system; (ii) by sequentially exposing the contents of the IFAC to the treatment agent, then after a preincubation period of contact with the agent, introducing the culture media and further incubating the sample with IBA acquisition of metabolic measures. In either case, comparison of the biocidel efficacy as well as effects on various enzyme systems can be measured to determine optimal treatment regimens.

Thus, the IFAC approach unexpectedly offers at least two key advantages for this approach: (i) it allows harvesting a sufficient volume of water containing "natural" organisms to obtain a representative sample of the population, and (ii) agents can be easily added to the IFAC, incubated under appropriate conditions and then washed out to culture the organisms under reproducible growth and assay conditions.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. An in vitro method for determining the presence and/or activity of biological material in a liquid sample, comprising the steps of:
   (i) filtering a liquid sample through an enclosed filter apparatus capable of trapping said biological material in said filter apparatus, whereby said biological material present in said liquid sample is retained in said filter apparatus;
   (ii) administering a reaction fluid into and/or through said filter apparatus, said reaction fluid comprising:
      i. components to support and/or affect the biological activity of said biological material and/or,
      ii. an indicator means for indicating the presence and/or activity of said biological material;
   (iii) incubating said filter apparatus, said biological material retained and said reaction fluid in a measurement apparatus;
   (iv) performing one or more measurements by optical means of said indicator means and/or said biological material concurrent with incubation of said biological material in said filter apparatus using said measurement apparatus; and
   (v) performing analysis of said measurements of the said indictor means and/or said biological material to determine activity of the said biological material,
   wherein steps (i)-(v) are performed within the enclosed filter apparatus.

2. The method according to claim 1, wherein said biological material comprises microorganisms, eukaryotic cells, or mixtures thereof.

3. The method according to claim 1, wherein said reaction fluid supports the growth of said biological material.

4. The method according to claim 1, wherein said filter apparatus enables the growth and formation of discrete colonies of said biological material.

5. The method according to claim 1, wherein said indicator means is incorporated into said filter apparatus prior to filtering said liquid sample.

6. The method according to claim 1, wherein said indicator means changes in response to a biologically induced gas change within said filter apparatus.

7. The method according to claim 1, wherein the means of filtering said liquid sample includes physical, chemical, and/or magnetic separation of said biological material from said liquid sample.

8. The method according to claim 1, wherein said measurement apparatus measures luminescence and/or color characteristics and/or changes therein of the indicator means.

9. The method according to claim 1, wherein said indicator means has fluorescent properties.

10. The method according to claim 1, wherein said indicator means has chromogenic properties.

11. The method according to claim 1, wherein said indicator means exhibits both fluorescent and chromogenic properties.

12. The method according to claim 1, wherein said indicator means relates to any approach whereby an optical signal is engendered indicating the presence, or identifying activity of the biological material.

13. The method according to claim 1, wherein said indicator means is a fluorogenic and/or chromomeric substrate reporter of $\beta$-galactosidase and said fluorogenic/chromogenic reporter comprises molecules chosen from resorufin-, 4-methylumbelliferyl-, ethyl-7-hydroxycourmarin-4-carboxylate, fluorescein-, 6-chloro-3-indoxyl (salmon), 5-bromo-4-chloro-3-hydroxyindoxyl- (X-), 6-Chloro-3-indoxyl- (salmon), 5-Bromo-6-chloro-3-indoxyl- (magenta-).

14. The method according to claim 1, wherein said indicator means is a fluorogenic and/or chromomeric substrate reporter of $\beta$-glucuronidase and said fluorogenic/chromogenic substrate reporter comprises molecules selected from the group consisting of resorufin-, 4-methylumbelliferyl-, ethyl-7-hydroxycourmarin-4-carboxylate, fluorescein-, 6-chloro-3-indoxyl (salmon), 5-bromo-4-chloro-3-hydroxyindoxyl- (X-), 6-Chloro-3-indoxyl- (salmon), and 5-Bromo-6-chloro-3-indoxyl- (magenta-).

15. The method according to claim 1, wherein said indicator means is a chemiluminogenic substrate reporter of $\beta$-galactosidase and said chemiluminogenic substrate reporter comprises a chemiluminogenic galactopyranoside chosen from families of 1,2-dioxetanes (AMPD-galactopyranoside).

16. The method according to claim 1, wherein said indicator means is a chemiluminogenic substrate reporter of $\beta$-glucuronidase and said chemiluminogenic substrate reporter comprises a chemiluminogenic glucuronide chosen from families of 1,2-dioxetanes.

17. The method according to claim 1, wherein said indicator means is a reporter of (β-galactosidase and detects fecal and/or total coliform bacteria.

18. The method according to claim 1, wherein said indicator means is a substrate reporter of β-glucuronidase and detects *E. coli*.

19. The method according to claim 1, wherein said biological material includes an indicator organism or organisms sensitive to the condition to be measured and said biological material being measurable by said indicator means.

20. The method according to claim 19, wherein said biological material indicates the effectiveness of a bactericidal agent.

21. The method according to claim 1 wherein changes in said indicator means are measured to determine characteristics of the biological sample indicative of said biological material's activity including initiation or inhibition of growth.

22. The method according to claim 21 wherein a change in said indicator means is measured during the sample incubation after a specified time and used as a measure of biological activity.

23. The method according to claim 21 wherein a single rate of change in said indicator means is determined during the sample incubation and used as a measure of biological activity.

24. The method according to claim 21 wherein rates of change in said indicator means are determined at several times during sample incubation, said rates used combinatorially as the measure of biological activity.

25. The method according to claim 21 wherein a change in rates of change in said indicator means is determined at a single time or multiple times as the measure of biological activity.

26. The method according to claim 21, further comprising determining the amount of said biological material in the liquid sample at the time of filtration by:
(vi) comparing the time at which a characteristic indicator-means change is detected in the test sample against the time required for a similar change to occur in known reference biological material; and
(vii) extrapolating the amount of biological material from a table or mathematical model based on said detection time.

27. The method according to claim 1, wherein said filter apparatus comprises:
(vi) a housing capable of holding a filter means within; and
(vii) a filter means capable of trapping said biological material in said housing,
wherein said housing allows (a) light from said measurement apparatus to penetrate said housing and (b) light from within the housing to exit said housing.

28. The method according to claim 27, wherein said housing comprises:
(viii) a closed chamber;
(ix) an inlet capable of passage of said liquid sample and said reaction media into and through said housing;
(x) a reservoir large enough to hold said filter means and said growth media;
(xi) an outlet capable of allowing passage of said liquid sample and said growth media out of said housing; and
(xii) a vent capable of allowing passage of gases in and out of said housing and capable of holding liquids within said housing.

29. The method according to claim 27, wherein said filter means comprises a porous filter element.

30. The method according to claim 29, wherein said filter element comprises polymeric membrane selected from the group consisting of nitrocellulose or mixed cellulose esters, polyether sulfone, nylon, polycarbonate, and polyvinylidenedifluoride (PVDF).

31. The method according to claim 29, wherein said filter element comprises cellulose, glass fibers, beads, or porous alumina.

32. The method according to claim 29, wherein said filter element comprises a filter capable of retaining said biological material of at least 0.2 microns.

33. The method according to claim 29, wherein said filter element has a pore size less than the size of said biological material.

* * * * *